(12) United States Patent
Doble et al.

(10) Patent No.: US 8,950,267 B2
(45) Date of Patent: Feb. 10, 2015

(54) METHODS AND APPARATUS FOR DETECTING CROSS-LINKING IN A POLYMER

(75) Inventors: Dan Doble, Somerville, MA (US); Rafal Mickiewicz, Cambridge, MA (US); John Lloyd, Boston, MA (US); Marco Jaeger, Freiburg (DE); William F. Hartman, Albuquerque, NM (US)

(73) Assignee: Fraunhofer USA, Inc., Plymouth, MI (US)

( * ) Notice: Subject to any disclaimer, the term of this patent is extended or adjusted under 35 U.S.C. 154(b) by 511 days.

(21) Appl. No.: 13/233,484

(22) Filed: Sep. 15, 2011

(65) Prior Publication Data

US 2012/0118071 A1 May 17, 2012

Related U.S. Application Data

(60) Provisional application No. 61/383,021, filed on Sep. 15, 2010.

(51) Int. Cl.
| | |
|---|---|
| *G01N 3/00* | (2006.01) |
| *G01N 11/00* | (2006.01) |
| *G01N 3/08* | (2006.01) |
| *G01N 3/40* | (2006.01) |
| *G01N 11/14* | (2006.01) |
| *H01L 31/048* | (2014.01) |

(52) U.S. Cl.
CPC ........ *G01N 3/40* (2013.01); *G01N 11/14* (2013.01); *G01N 2203/0092* (2013.01); *H01L 31/048* (2013.01)
USPC .................................. 73/788; 73/818; 73/790

(58) Field of Classification Search
CPC ............ G01N 3/08; G01N 2203/0019; G01N 2203/0094
USPC .................................. 73/788, 818, 790
See application file for complete search history.

(56) References Cited

U.S. PATENT DOCUMENTS

| | | | |
|---|---|---|---|
| 6,500,295 B1 | 12/2002 | Kubota | |
| 7,509,881 B2 * | 3/2009 | Divigalpitiya et al. | .. 73/862.041 |

(Continued)

FOREIGN PATENT DOCUMENTS

EP 0264055 A2 * 4/1988

OTHER PUBLICATIONS

International Search Report & Written Opinion from.PCT/US11/51737, mailed Feb. 3, 2012.

(Continued)

*Primary Examiner* — Lisa Caputo
*Assistant Examiner* — Jonathan Dunlap
(74) *Attorney, Agent, or Firm* — Wolf, Greenfield & Sacks, P.C.

(57) ABSTRACT

Methods and apparatus for detecting cross-linking in a polymer, wherein, in some exemplary implementations, the polymer may constitute an encapsulation layer for a photovoltaic module. In one example, a polymer sample is physically deformed, and sample information relating to a relaxation or a recovery of the polymer sample in response to the deformation is obtained. The sample information is then compared to reference information relating to cross-linking of the polymeric material so as to determine a degree of cross-linking in the tested polymer sample. In one aspect, such a determination of polymer cross-linking is achieved without adversely affecting a relevant functionality of the polymer/encapsulation layer (e.g., without destruction to the polymer/encapsulation layer).

45 Claims, 19 Drawing Sheets

(56) References Cited

U.S. PATENT DOCUMENTS

| | | | |
|---|---|---|---|
| 2006/0243035 A1* | 11/2006 | Aoki | 73/105 |
| 2009/0158826 A1 | 6/2009 | Leroux | |
| 2010/0139413 A1 | 6/2010 | Herrmann et al. | |
| 2012/0085155 A1* | 4/2012 | Guerout et al. | 73/82 |
| 2012/0271555 A1* | 10/2012 | Levental et al. | 702/19 |

\* cited by examiner

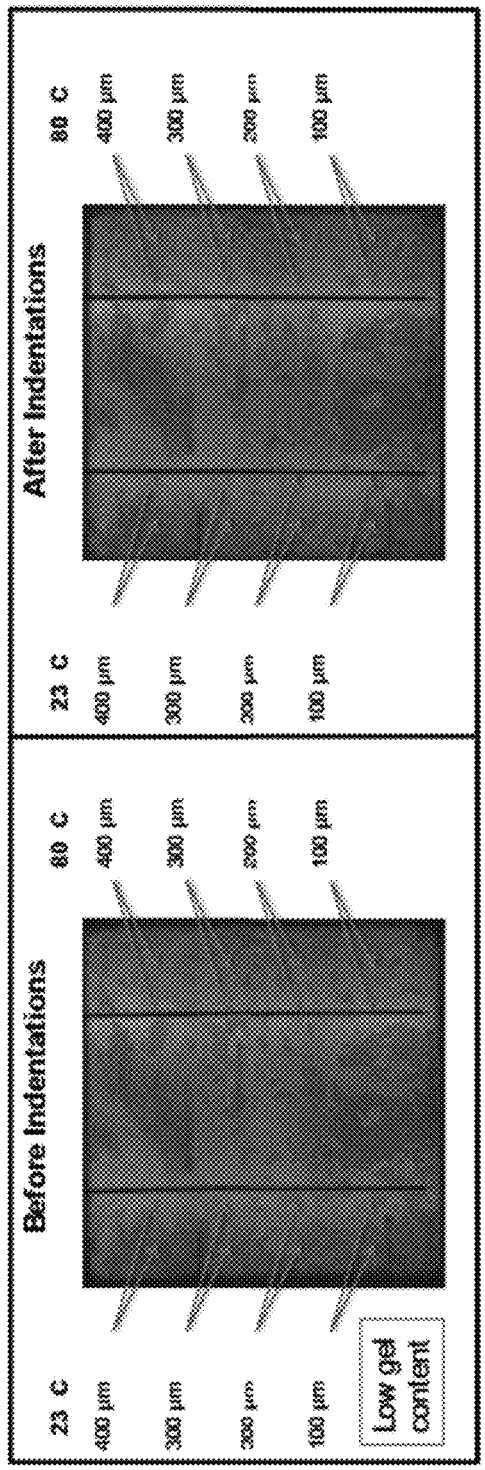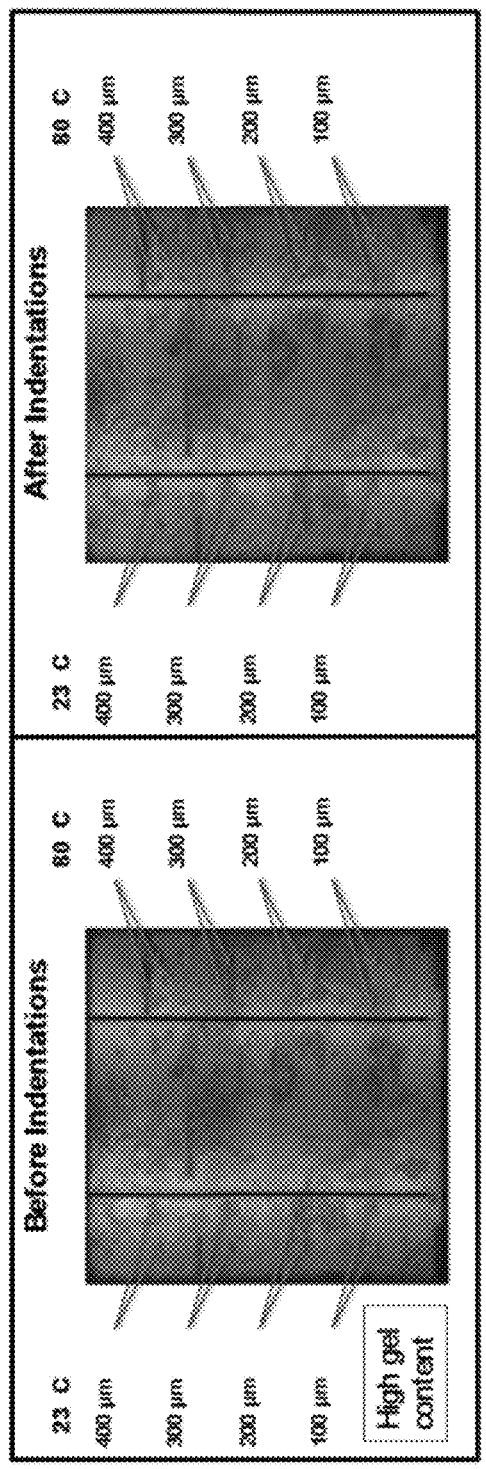
Fig. 25
Fig. 26
Fig. 27
Fig. 28

METHODS AND APPARATUS FOR DETECTING CROSS-LINKING IN A POLYMER

RELATED APPLICATIONS

This application claims priority to U.S. Provisional Patent Application Ser. No. 61/383,021, filed Sep. 15, 2010 which is incorporated herein by reference in its entirety.

BACKGROUND

Direct conversion of solar energy to electrical energy can provide a virtually unlimited source of clean energy. Solar cells fabricated from semiconductor materials have been refined through years of research, and are commonly assembled in arrays to form photovoltaic modules for harvesting and converting solar energy to electrical energy. Conventional photovoltaic modules typically include a stack of materials including at least one encapsulation layer. The encapsulation layer is added to protect the photovoltaic module from the environment, and to provide electrical insulation of the module. One example of a conventional material often employed as an "encapsulant" for use in the encapsulation layer is ethylene vinyl acetate (EVA) copolymer.

The lamination process is an important step in the photovoltaic module manufacturing process, during which the silicon cells are laminated with one or more encapsulation layers and packaged in their final form before shipment. During an exemplary conventional lamination process, EVA is applied to a photovoltaic module and the EVA is cured so as to promote cross-linking to prevent creeping of the encapsulation layer(s) as a result of temperature or stress. Since the cross-linking reaction of the EVA is irreversible, cell reclamation is impossible should anything go wrong with the lamination/curing process. Therefore, extreme care is taken to ensure that the lamination conditions are set correctly in order to guarantee continuous production of reliable and durable modules, which meet international certification standards.

Improperly laminated modules often may develop defects leading to premature failures and the inevitable loss in module performance. For example, incompletely cured encapsulant retains its thermoplastic behavior, resulting in flowing or creeping when exposed to solar heat. Excessive flow may result in mechanical failure of the encapsulant, exposing the silicon cells to the outdoor environment, which could lead to electrical faults, cell or interconnection cracking, and corrosion. Additionally, poor adhesion or bubbles in the encapsulant may lead to optical losses in the solar module. On the other hand, EVA that is fully cured no longer flows, offers excellent resistance to creep, and ensures proper bonding of the encapsulant within the module.

The level of curing in EVA is correlated with the degree of polymer cross-linking that occurs during the lamination process. Two conventional methods commonly used for detection of the degree of cross-linking of EVA include the "gel fraction" test and the "creep" test. Unfortunately, both techniques involve destruction of the module. In the case of the gel fraction test, two days and wet chemistry lab capabilities are needed to complete the procedure. Another method for assessing polymer cross-linking includes a differential scanning calorimetry (DSC) technique developed by BP Solar. However, this technique offers limited resolution and has not been widely applied. Another limitation of the DSC technique is that it relies on knowledge of the thermal history of the sample (i.e. whether it had previously been cured, as well as the amount of time at elevated temperature). Furthermore, this technique also requires the destruction of a photovoltaic module to obtain the material needed for testing.

SUMMARY

The inventors have recognized and appreciated a need for improved measurement techniques for determining a level of encapsulant curing in photovoltaic modules to assess a post-lamination quality of such modules. More generally, the inventors have recognized various advantages to non-destructive techniques for determining a degree of cross-linking in polymer materials, especially in circumstances in which such materials are performing relevant functionality in situ in connection with other materials and/or components of a device in which they are employed.

In view of the foregoing, various inventive embodiments disclosed herein relate to improved methods and apparatus for determining a degree of cross-linking in polymer materials. In various aspects, the polymer materials may be "stand-alone" polymer samples, or be polymer samples that are employed alone or together with other materials (e.g., as a layer or laminate) as part of a device. In exemplary embodiments, a relaxation or recovery process of a polymer sample in response to physical deformation of the polymer sample is observed and measured, and information relating to the relaxation or recovery process is compared to reference information relating to cross-linking of the polymer. In this manner, a degree of cross-linking in the polymer sample may be assessed. In other aspects, such an assessment may be performed without adversely affecting a relevant functionality of the polymer material (e.g., without destruction to the polymer material and/or a device in which the polymer material is employed).

In one exemplary embodiment, the polymer sample constitutes at least a portion of an encapsulation layer for a photovoltaic module, and a degree of cross-linking of the encapsulation layer may be assessed without adversely affecting the performance of the photovoltaic module or destroying the photovoltaic module. In one aspect, such an assessment may be performed in situ or "in line" with a lamination process for the photovoltaic module, during which an encapsulant is applied to the module, cured, and tested for completeness of curing (i.e., degree of cross-linking of the polymer material). Alternatively, such an assessment may also be incorporated inside of or as part of a laminator. As noted above, in exemplary implementations involving photovoltaic modules, one example of a polymeric material for which a degree of cross-linking may be determined according to the inventive methods and apparatus disclosed herein is given by EVA.

In sum, one embodiment of the present invention is directed to a method for detecting cross-linking in a polymer sample, the method comprising: A) physically deforming a polymer sample using a tester; B) obtaining sample information relating to a relaxation or a recovery of the polymer sample in response to A); and C) comparing the sample information to reference information relating to the cross-linking so as to determine a degree of the cross-linking in the polymer sample.

Another embodiment relates to an apparatus for detecting cross-linking in a polymer sample includes a tester and a processor. The tester includes at least a first and second component. The first component physically deforms the polymer. The second component obtains sample information regarding the physical response of the polymer due to the deformation of the first component. The processor compares the sample information from the second component to reference information relating to the cross-linking in the polymer. The comparison between the sample information and reference information determines the degree of cross-linking present in the polymer.

Another embodiment relates to a method for detecting cross-linking in an ethylene vinyl acetate film, the method comprising: physically deforming the film using a tester; obtaining sample information related to a relaxation or recovery of the film in response to the deformation; and comparing the sample information to reference information relating to the cross-linking in the film. The comparison between the sample information and reference information determines the degree of cross-linking present in the film.

Another embodiment related to an apparatus for detecting cross-linking in ethylene vinyl acetate includes a tester and a processor. The tester includes at least a first and second component. The first component physically deforms an ethylene vinyl acetate film. The second component obtains sample information regarding the physical response of the film due to the deformation of the first component. The processor compares the sample information from the second component to reference information relating to the cross-linking in the film. The comparison between the sample information and reference information determines the degree of cross-linking present in the film.

In exemplary implementations of the embodiments introduced above and discussed in further detail below, faster non-destructive techniques for assessing polymer curing are realized. In the context of photovoltaic module production, these techniques enable improved module quality control and end point detection for increased throughput and process repeatability. Additionally, such techniques not only significantly improve module reliability and long-term efficiency, but also reduce manufacturing costs, thereby reducing overall system and operation cost.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

The foregoing and other aspects, embodiments, and features of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

FIG. 25 shows an electroluminescence image of a mini-module with a low gel content encapsulant prior to a series of indentation measurements;

FIG. 26 shows an electroluminescence image of a mini-module with a low gel content encapsulant after a series of indentation measurements;

FIG. 27 shows an electroluminescence image of a mini-module with a high gel content encapsulant prior to a series of indentation measurements; and FIG. 28 shows an electroluminescence image of a mini-module with a high gel content encapsulant after a series of indentation measurements.

DETAILED DESCRIPTION

Introduction

Figure 1:
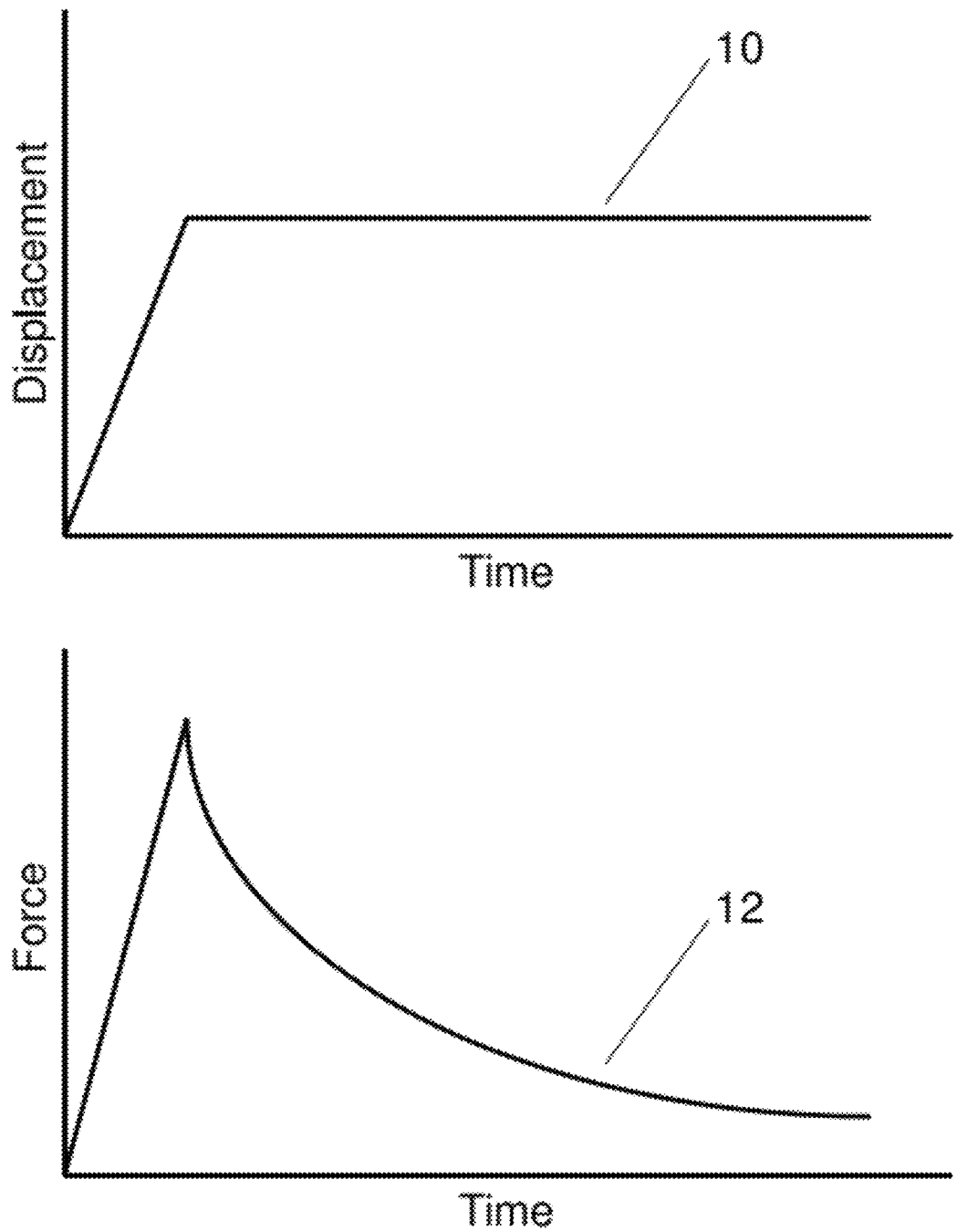
FIG. 1 shows exemplary force and displacement profiles for a relaxation process.

Following below are more detailed descriptions of various concepts related to, and embodiments of, inventive systems, methods and apparatus for detecting cross-linking in a polymer, and assessing a degree of cross-linking or gel content in a polymer sample (e.g., subject to a curing process). It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As it relates to the discussion below, the terms "gel fraction", "gel content", "cross-linking level", and "degree of cross-linking" may be used interchangeably. Strictly speaking though, whenever a numerical value is given in regards to the above, it is the gel content or gel fraction as determined by solvent extraction with toluene. Therefore, the numerical values quoted do not necessarily correspond to a degree of cross-linking or cross-linking level. However, it should be noted that a sample with a high gel content is more highly cross-linked, and this is what the gel content test is assessing. In other words, the test does not measure a percentage of cross-linking level. Instead, it measures the gel content of the material which is related to the degree of cross-linking in the material.

In various embodiments discussed in greater detail below, generally a polymer sample is physically deformed, and sample information relating to a relaxation or a recovery of the polymer sample in response to the deformation is obtained. The sample information is then compared to reference information relating to cross-linking of the polymeric material so as to determine a degree of cross-linking in the tested polymer sample. In one aspect, such a determination of polymer cross-linking is achieved without adversely affecting a relevant functionality of the polymer material and/or an associated construction or device (e.g., without destruction of the polymer material, construction, or device).

Polymers, such as EVA, exhibit viscoelastic properties, where the mechanical response of the polymer is dependent on the rate or time period of loading or deformation. Viscoelastic materials, therefore, exhibit two distinct responses to an applied force or displacement, an elastic (or Hookean) response and a viscous (Newtonian or non-Newtonian flow) response. If the force or displacement is small and applied over a sufficiently short period of time the material will behave like an elastic solid. Conversely, if the force or displacement is large and applied over a sufficiently long period of time the material will flow and accommodate the applied force or displacement in what is known as a relaxation process. This ability of the material to flow is due to the atoms and molecules being able to rearrange. The time periods over which these two distinct behaviors occur is related in part to the viscosity of the material. A high viscosity results in a material with a slow relaxation process. Furthermore, a material with a high viscosity behaves much like an elastic solid due to the slower relaxation process. Conversely, a lower viscosity results in a faster relaxation process and a material that behaves less like an elastic solid.

Polymers may exhibit a "shape memory" like behavior. This behavior is due to the tendency of strained polymer chains to relax to their equilibrium coil dimensions. Upon removal of an external force or displacement from the polymer, entangled polymer chains will tend to partially retract and return to their original shape and position. This "shape memory" like effect results in a what is known as a recovery process. The rate at which this recovery process occurs is again related to the viscosity of the material. Similar to above, the lower the viscosity of the material the faster the recovery process.

FIG. 1 shows an example of a relaxation process in which a viscoelastic material is subjected to a sudden and constant applied displacement 10. The force 12 initially rises in response to the increasing material displacement 10. When the displacement 10 reaches its final constant value force 12 reaches a peak value and then begins to exponentially decay. This is due to the ability of the viscoelastic material to flow and accommodate an applied force or displacement.

Figure 2:
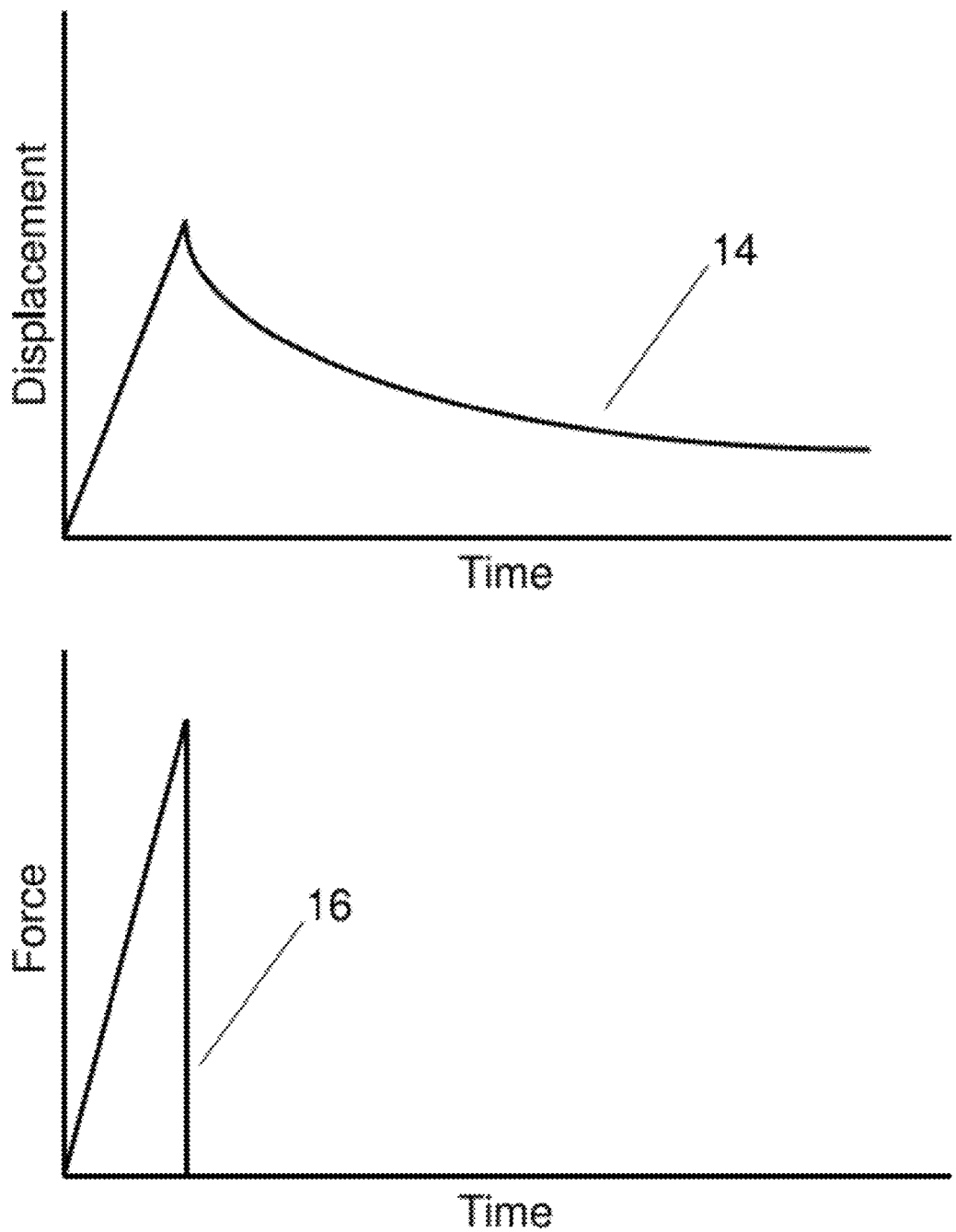
FIG. 2 shows exemplary force and displacement profiles for a recovery process.

FIG. 2 shows an example of a recovery process in which a viscoelastic material is suddenly deformed to a given displacement 14 or force 16 prior to removing force 16. After removing force 16 the material is able to recover a portion of the applied material displacement 14, but this recovery does not occur immediately. As described above for a relaxation process, this recovery of displacement 14 exhibits an exponential decay.

As previously noted, the rates of relaxation and recovery processes is in part related to the viscosity of a material. A lower material viscosity results in a faster rate of decay. Conversely, a larger material viscosity results in a slower rate of decay. The viscosity of a polymer is related to several different properties including the ability of the polymer chains to slide past one another. This ability to slide past one another allows the polymer chains to rearrange and accommodate an applied force or displacement. The more easily individual polymer chains slide past one another the lower the polymer viscosity will be. As polymer chains become more entangled with one another, they are not able to easily slide past one another and the polymer viscosity increases. In certain polymers, such as EVA, cross-links are formed between separate polymer chains. These cross-links between polymer chains inhibit the free rearrangement and flow of the individual polymer chains and consequently result in a higher viscosity, ultimately resulting in a material that cannot flow at high levels of cross-linking. In light of the above, one would expect the degree of cross-linking to influence the decay rates for relaxation and recovery processes.

It is possible to quantify the decay rates for relaxation and recovery processes by the use of at least one relaxation time constant. A smaller time constant corresponds to a faster decay rate and lower viscosities. A larger time constant corresponds to a slower decay rate and higher viscosities. Since cross-linking raises viscosity by inhibiting the flow of viscoelastic polymers, such as EVA, an increasing relaxation time constant should correlate with an increasing degree of cross-linking.

With consideration of the foregoing, the inventors have developed an alternative approach to determining the degree of cross-linking in a polymer. Various embodiments of the present invention are directed to extracting sample information regarding viscoelastic properties from the relaxation and recovery responses of a polymer sample and comparing that sample information to reference information relating to a degree of cross-linking. The various embodiments of the methods and apparatus for detecting cross-linking in a polymer are described further in the following sections.

Calculations

In one embodiment, sample information comprises the material's relaxation time constant. The relaxation time constant may be calculated using a simple mechanical model of a relaxation process incorporating a spring, with a spring constant E (corresponding to the elastic modulus), placed in series with a dashpot, with damping η (corresponding to the viscosity) and subjected to a constant displacement. The relaxation function is shown in Equation 1, where σ(t) is the time dependent stress, $\sigma_0$ is the initial stress, t is time, and τ is the material dependent characteristic relaxation time constant (τ=η/E).

$$\sigma(t) = \sigma_0 e^{\frac{-t}{\tau}} \quad (1)$$

This simple model is known as the Maxwell model. In some embodiments this model can be extended to more complex systems by placing several dashpot-spring pairs in parallel. This so-called "Generalized Maxwell Model" reflects more complex materials that exhibit several independent relaxation time constants.

$$\sigma(t) = \sigma_1 e^{\frac{-t}{\tau_1}} + \sigma_2 e^{\frac{-t}{\tau_2}} + \ldots \quad (2)$$

In the current example of the Maxwell model, the relaxation time constant is determined by fitting a linear trendline to the relation between the natural log of the decaying function with the corresponding test time. This fitting may be accomplished either graphically or computationally. While a single constant linear fit to the log plot of σ(t) has been disclosed, the current embodiment is not limited in this fashion. It is also possible to fit multiple time constants using any number of appropriate methods. In some instances multiple time constants may be determined using a fit to the exponential curve.

It is within the scope of this disclosure to model the relaxation time constants using any one of a number of physical models in addition to the Maxwell model described above. One other exemplary model includes the Voigt-Kelvin model which may be applied to determining relaxation time constants for recovery processes. In another embodiment, an oscillating deformation, as described further below, is applied to the polymer sample to determine the storage and loss characteristics of the material. When performing such a test, the dynamic viscosity of the material may be obtained by dividing the shear loss modulus by the angular frequency of the sinusoidal oscillation, i.e. η'=G"/ω.

While the above description of the Generalized Maxwell Model and the Voigt-Kelvin model has been directed to the stress or strain relaxation processes, respectively, in order to determine one or more relaxation time constants, alternative methods of analyzing the viscoelastic nature of the material may be used as well. For example, instead of computing one or more relaxation time constants, the relaxation or recovery behavior of the material may be monitored and evaluated by measuring and quantifying the change (decay) in the force or displacement over a specified amount of time. In addition, one of skill in the art would recognize that the Generalized Maxwell Model and Voigt-Kelvin model may be applied to any relaxation process present in the system that would be of interest as the current disclosure is not limited in this fashion.

Example 1

Method and Apparatus for Detecting Cross-Linking in a Polymer

Figure 3A:
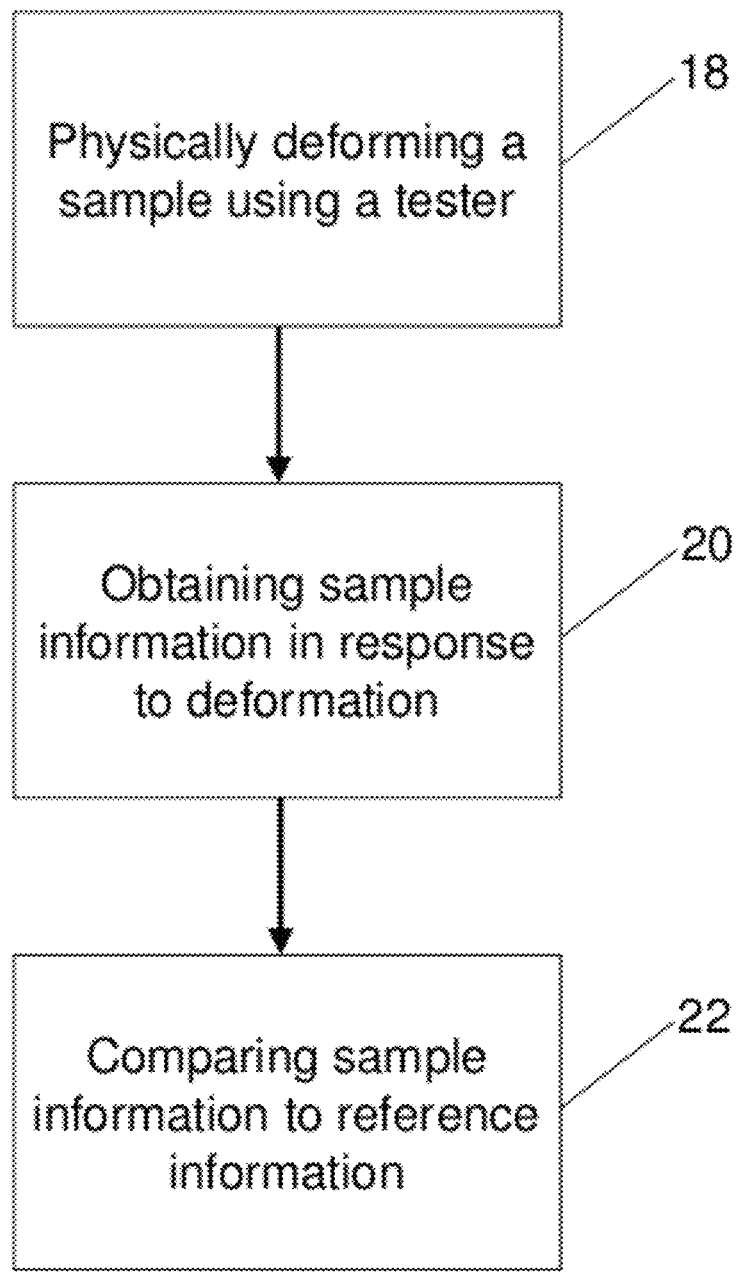
FIG. 3A shows an exemplary flow chart of a method for determining the degree of cross-linking in a polymer according to one embodiment of the present invention.

FIG. 3A shows a method for determining the degree of cross-linking in a polymer. The method includes physically deforming 18 a sample using a tester and obtaining 20 sample information relating to either a relaxation or recovery process of the deformed polymer sample. The method further includes comparing 22 the sample information to reference information relating to a degree of cross-linking in the polymer. Since a material's viscosity and corresponding relaxation time constant are dependent on temperature, it may be desirable to perform testing at an elevated temperature in some embodiments.

Figure 3B:
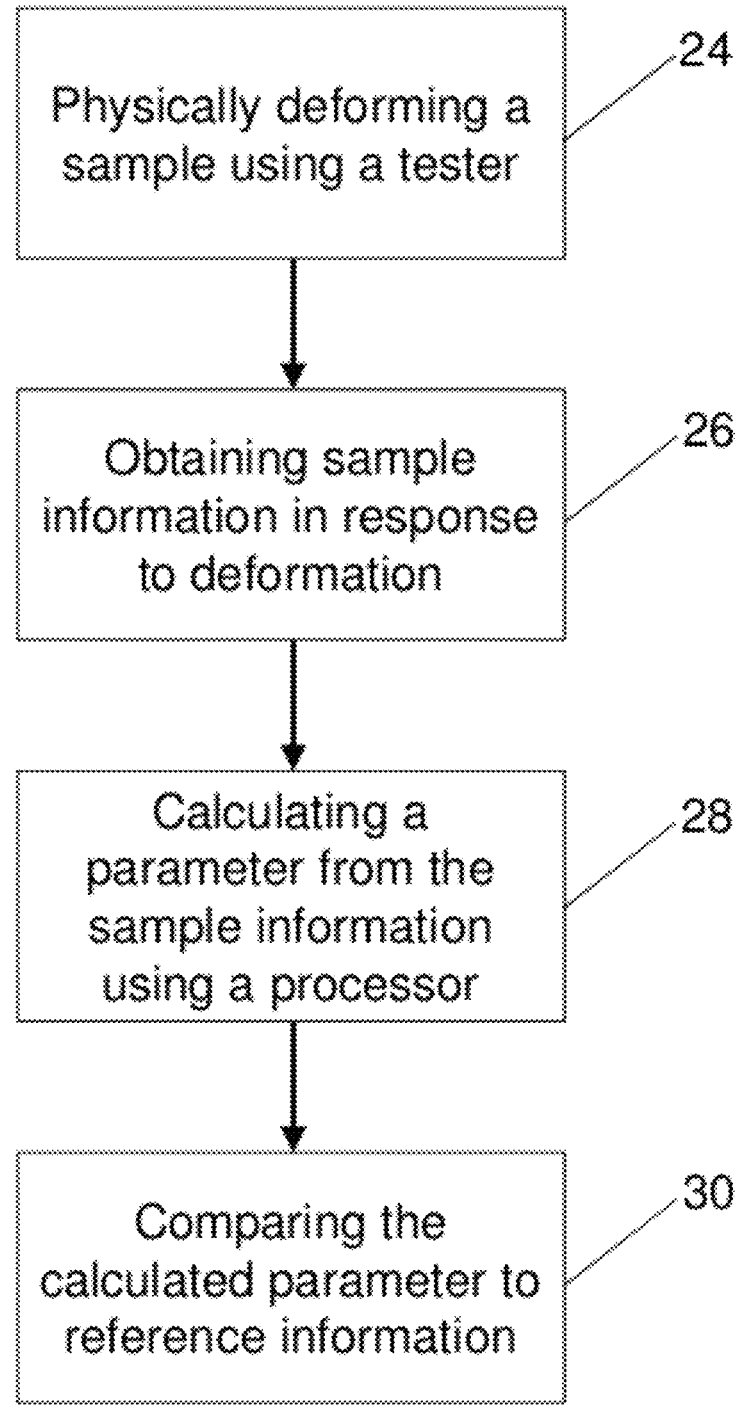
FIG. 3B shows an exemplary flow chart of a method for determining the degree of cross-linking in a polymer according to another embodiment of the present invention.

FIG. 3B shows a method for determining the degree of cross-linking in a polymer. The method includes physically deforming 24 a sample using a tester and obtaining 26 sample information relating to either a relaxation or recovery process of the deformed polymer sample. The method further includes calculating 28 a parameter from the sample information using either a computer or processor. The method also includes comparing 30 the calculated parameter to reference information relating to a degree of cross-linking in the polymer. Since a material's viscosity and corresponding relaxation time constant are dependent on temperature, it may be desirable to perform testing at an elevated temperature in some embodiments.

A test as described above for FIGS. 3A and 3B has several advantages over the prior art. Such a test may be incorporated in line with a laminator or other machine during a manufacturing process. It may also be incorporated directly inside of or as a part of a laminator. The described test also is relatively quick compared to widely accepted testing methods. Furthermore, the currently described test can be performed in a non-destructive fashion. This is in contrast to current methods requiring lengthy testing procedures, the sacrifice of a product to test the degree of cross-linking, or both.

The methods as described above are generally directed to determining a degree of cross-linking in polymers. One possible application of the above testing methods is for measuring the degree of cross-linking in an EVA encapsulation film on a photovoltaic module.

Example 2

Apparatus for Detecting Cross-Linking in a Polymer

Figure 4:
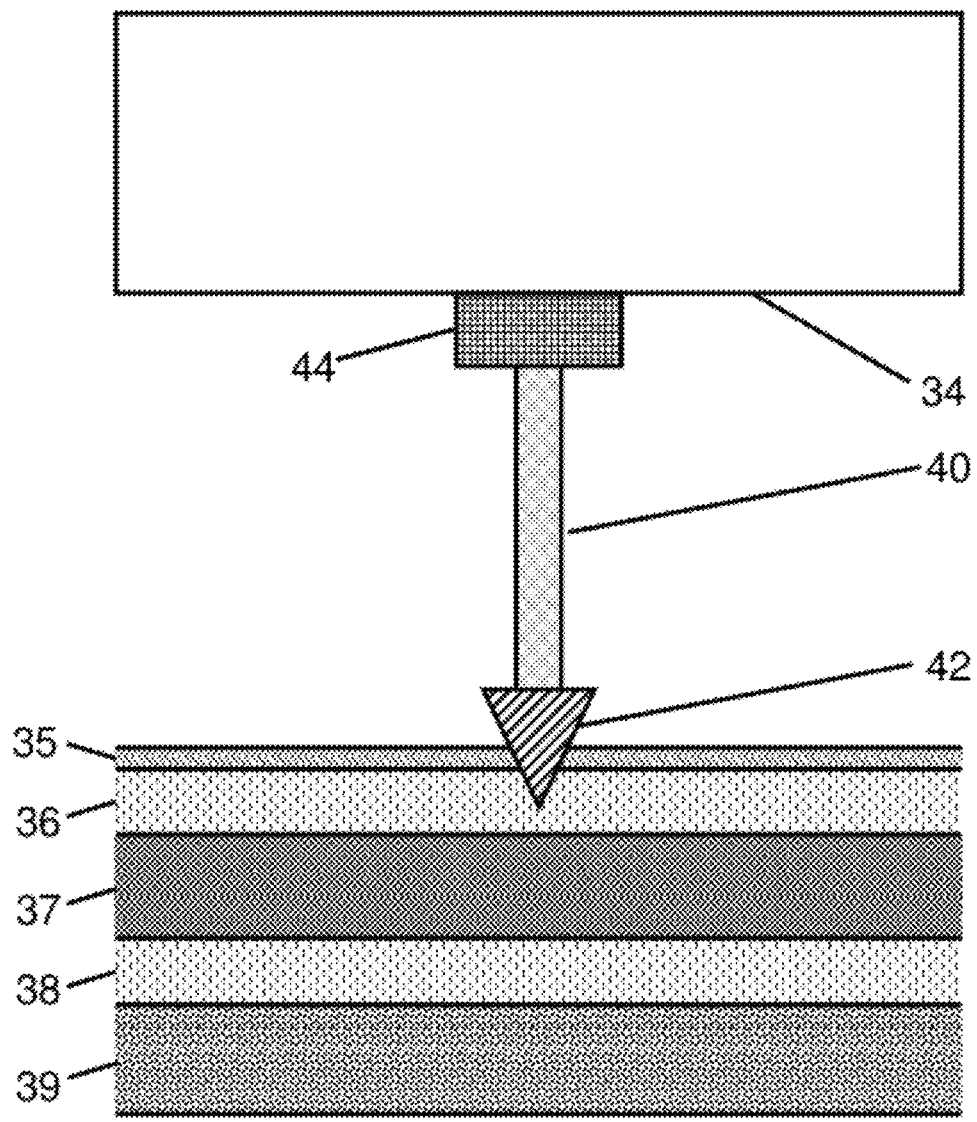
FIG. 4 shows a schematic representation of a tester and a photovoltaic module during a relaxation or recovery test according to one embodiment of the present invention.

In one embodiment, the methods of FIGS. 3A and 3B may be implemented for a relaxation process, a recovery process, or a combination of both processes using a tester 34 as depicted in FIG. 4. FIG. 4 shows a tester 34 and a portion of a photovoltaic module in cross-section. The depicted portion of the photovoltaic module comprises a thin back layer 35, a first layer 36 of encapsulating EVA film, a photovoltaic cell 37, a second layer 38 of the encapsulating EVA film, and glass 39. In typical solar cell constructions, the polyester used in the back layer is predominantly polyethylene terephthalate (PET). However, the current disclosure is not limited to any particular polymer composition of either the encapsulating films or back layer. Instead, the current disclosure should be broadly interpreted as applying to any cross-linking polymer or component including a cross-linking polymer.

In exemplary implementations, the thin back layer 35 may comprise a tri-laminate film of Tedlar-Polyester-Tedlar ("TPT") (Tedlar is the DuPont trade name for poly(vinyl fluoride) (PVF)). In other implementations, one or more of the Tedlar constituents of the thin back layer may be replaced with EVA (e.g., a tri-laminate thin back layer film of Tedlar-Polyester-EVA or "TPE"), or aluminum may be employed as a constituent element (e.g., a tri-laminate thin back layer of Tedlar-Aluminum-Polyester or "TAP"). In yet other implementations, the thin back layer 35 may comprise a single layer/single material film of Tedlar, Polyester, or some other material. Generally, the thickness of the thin back layer 35 is below 200 um (e.g., in the range of from approximately 120 um to 150 um). In practice, the back layer 35 is significantly thinner than the layer 36 of encapsulating EVA film, and methods described herein to determine one or more properties of the layer 36 are performed in a manner such that the contribution of thin back layer 35 to one or more measured properties of the layer 36 of encapsulating EVA film can be essentially neglected or decoupled from the measurement. While particular dimensions and materials have been cited above, it should be recognized that disclosure is not limited to any specific material and/or physical construction.

As illustrated in FIG. 4, the tester may comprise a first component 40 to physically deform the first layer 36 of the EVA film and a second component 44 to obtain information regarding the response of the first layer 36 to the deformation. The tester 34 may further include a processor (not shown specifically in FIG. 4) used to compare the information obtained by the second component to reference information related to a degree of cross-linking in the film 36. This measurement and comparison may allow a user to determine the degree of cross-linking in the film quickly and accurately.

As described above, the first component 40 physically deforms film layer 36. In certain embodiments, the first component 40 further includes an indenter head 42 that directly contacts the film layer 36. In some embodiments, the indenter head 42 may preferably be a truncated 30° wedge, a dome, a pyramid, or any other appropriate geometry. The indenter head 42 may be displaced into thin back layer 35 and film layer 36 by the use of any appropriate method. Testers of this type may incorporate either a shaft or a base member to which the indenter head 42 is mounted. The shaft or base member is then displaced in a controlled manner using a stepper motor, linear drive, or any other device that produces a controllable linear displacement. In some embodiments, the displacement may be an oscillatory displacement.

Figure 5:
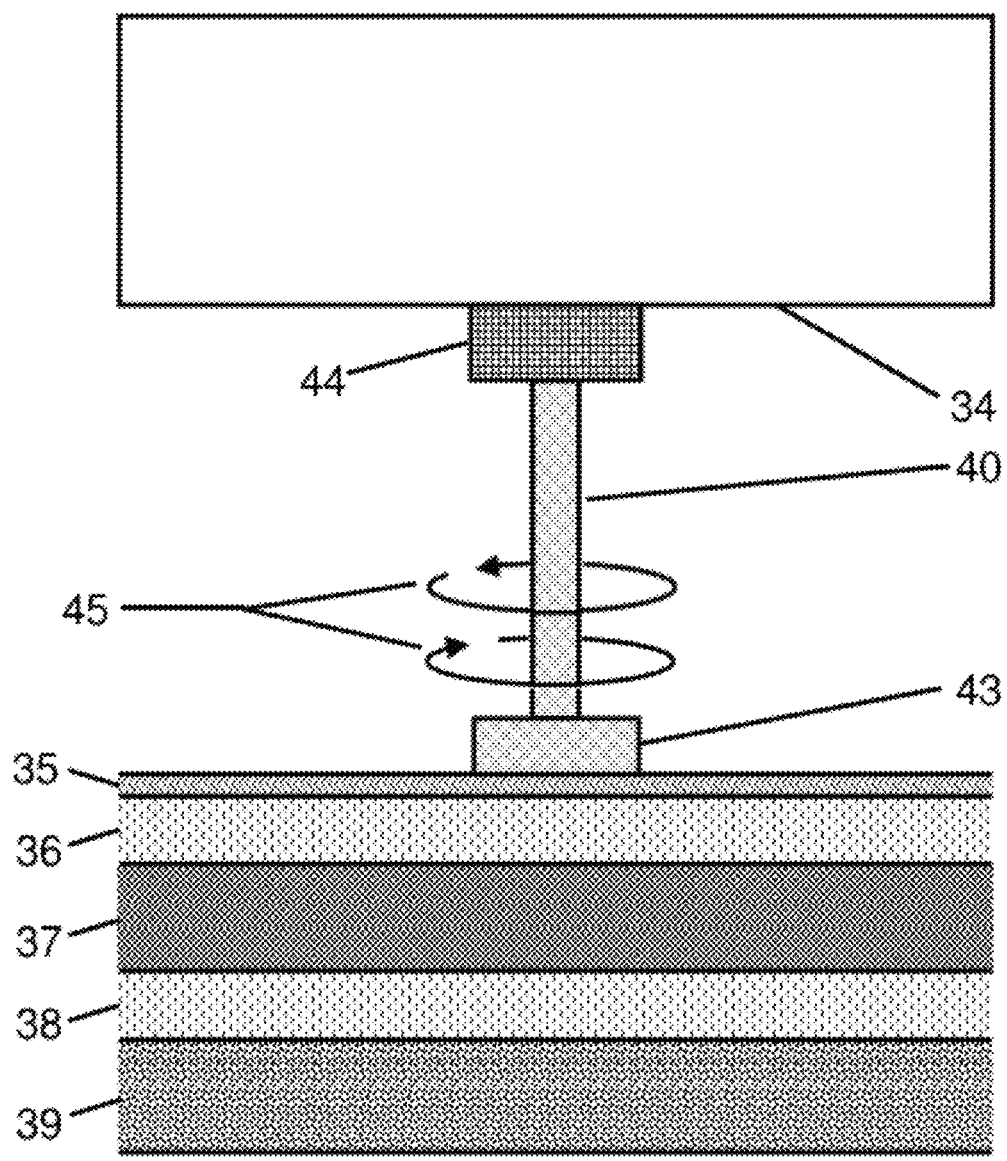
FIG. 5 shows a schematic representation of a tester and a photovoltaic module during dynamic mechanical analysis testing according to one embodiment of the present invention.

In certain other embodiments, as illustrated in FIG. 5 and discussed in greater detail below, the first component 40 physically deforms the film in an oscillatory shear fashion in the plane of the film, either by means of a torsional motion or a linear motion. During the oscillatory deformation, the applied force and/or displacement may be monitored as a function of time. In some implementations, the indenter head 42 of the device shown in FIG. 4 may be replaced by another element suitable for effecting oscillatory shear (e.g., a flat circular platen or other platen shapes).

With reference again to FIG. 4, the second component 44 of the tester obtains sample information relating to the relaxation or recovery response of film 36 by measuring at least one of displacement and/or force monitored as a function of time. Displacement measurements may be made using extensometers, linear voltage displacement transducers, strain gauges, laser interferometers, or any other appropriate displacement gauge. Force measurements may be made using load cells, mechanical gauges, or any other appropriate force gauge. The measured displacements and forces may alternatively be expressed as stress or strain of the sample through simple mathematical conversions. Therefore, it should be understood that whenever the terms displacement or force are used, stress or strain could be used instead.

As noted above, in certain embodiments, tester 34 includes or is communicatively coupled to a processor. The processor compares the sample information obtained by the second component 44 to reference information relating the physical response of film 36 with a degree of cross-linking (while not shown explicitly in FIG. 4, in addition to one or more processors the tester 34 may include or be communicatively coupled to one or more memory devices in which the sample information and/or reference information relating to polymer cross-linking may be stored, and/or one or more communication interfaces for receiving/transmitting the reference information and/or sample information). In some embodiments, the processor computes at least one relaxation time constant, as detailed above, from the sample information obtained by the second component 44 prior to comparison with the reference information. After calculating at least one relaxation time constant, the processor compares the calculated relaxation time constant with the reference information. The reference information may be in the form of an equation, a reference table, or any other appropriate format. Furthermore, as noted above, the processor may be located internally or externally to tester 34. In some embodiments the processor may control the tester in addition to comparing the measured sample information with the reference information.

The above description and FIGS. 4-7 describe methods and systems for measuring a degree of cross-linking which may be utilized in connection with an EVA encapsulation film on a photovoltaic module, as well as other types of polymers and/or other devices in which polymers are employed. In particular, it should be understood that the apparatus and methods described herein may be suitably adapted and applied to measuring a degree of cross-linking for polymers in general in various contexts. Furthermore, the reference information necessary to determine the degree of cross-linking may be different for different classes of polymers (i.e. the response of a cross-linked EVA is different from the response of a vulcanized rubber).

Example 3

Relaxation Testing

In one embodiment the methods depicted in FIGS. 3A-3B and the apparatus of FIG. 4 are applied to a relaxation test similar to the example depicted in FIG. 1. A sudden displacement is applied to a polymer sample and maintained at a final constant value. In some embodiments the polymer sample is deformed to an approximate depth of 100 μm. In other embodiments, the indentation depth may be approximately 200 μm, 300 μm, 400 μm, or any other appropriate depth. The resulting force from indentation initially peaks and subsequently decays through a relaxation process. However, this decay does not occur instantaneously. Instead, the decay proceeds at a rate determined by the relaxation time constant previously described. As detailed above, the relaxation time constant is expected to increase with an increasing degree of cross-linking in the polymer. Consequently, it is possible to determine the degree of cross-linking present in the polymer sample by comparing the sample information with the reference information. In certain embodiments the sample information may either be a calculated value such as the relaxation time constant or it may be the raw data. The raw data may include force and/or displacement data monitored and recorded as a function of time.

Example 4

Recovery Testing

In another embodiment the methods depicted in FIGS. 3A-3B and the apparatus of FIG. 4 are applied to a recovery test similar to the example depicted in FIG. 2. A sudden force or displacement is applied to a polymer sample. Once the maximum force or displacement is reached the force or component deforming the polymer sample is removed. In some embodiments the polymer sample is deformed to an approximate depth of 100 µm prior to removal of the force or component. In other embodiments, the indentation depth may be approximately 200 µm, 300 µm, 400 µm, or any other appropriate depth. As described above a portion of the total displacement is recoverable by the polymer sample. However, this recovery does not occur instantaneously. Instead, the recovery proceeds at a rate determined by the relaxation time constant previously described. As detailed above, the relaxation time constant is expected to increase with an increasing degree of cross-linking in the polymer sample. Consequently, it is possible to determine the degree of cross-linking present in the polymer sample by comparing the sample information with the reference information. In certain embodiments the sample information may either be a calculated value such as the relaxation time constant or it may be the raw data. As noted above, the raw data may include force and/or displacement data monitored and recorded as a function of time.

Example 5

Dynamic Mechanical Analysis Testing

In another embodiment, sample information comprises the storage modulus, loss modulus, and damping (tan(δ)). This data may be obtained from a dynamic mechanical analysis (DMA) where a small sinusoidal force is applied and the resulting sinusoidal displacement is measured. When operated in the shear mode (either torsion or linear), the dynamic viscosity of the material can be obtained by dividing the shear loss modulus by the angular frequency of the sinusoidal oscillation, i.e. $\eta'=G''/\omega$. Since the extent of cross-linking will have an effect on the material viscosity, as outlined above, these measurements can be used to determine the level of cure of the film 36. Furthermore, the degree of cross-linking is also expected to have an effect on the polymer modulus and this will be reflected in the value of the shear storage modulus.

FIG. 5 shows one embodiment of an apparatus capable of performing the above DMA test. The apparatus is similar to that depicted in FIG. 4. However, instead of having an indenter head 42, this apparatus has a platen 43 in contact with the sample. In the depicted embodiment, platen 43 applies a sinusoidal shear force via an oscillating rotation depicted by arrows 45. In other embodiments, platen 43 may apply an oscillating shear force by translational movement parallel to the surface of the sample instead of rotational movement. In one preferred embodiment platen 43 is a circular plate. However, platen 43 may be any appropriate shape capable of applying a shear force to the sample.

Example 6

Non-Contact Recovery Testing

Figure 6:
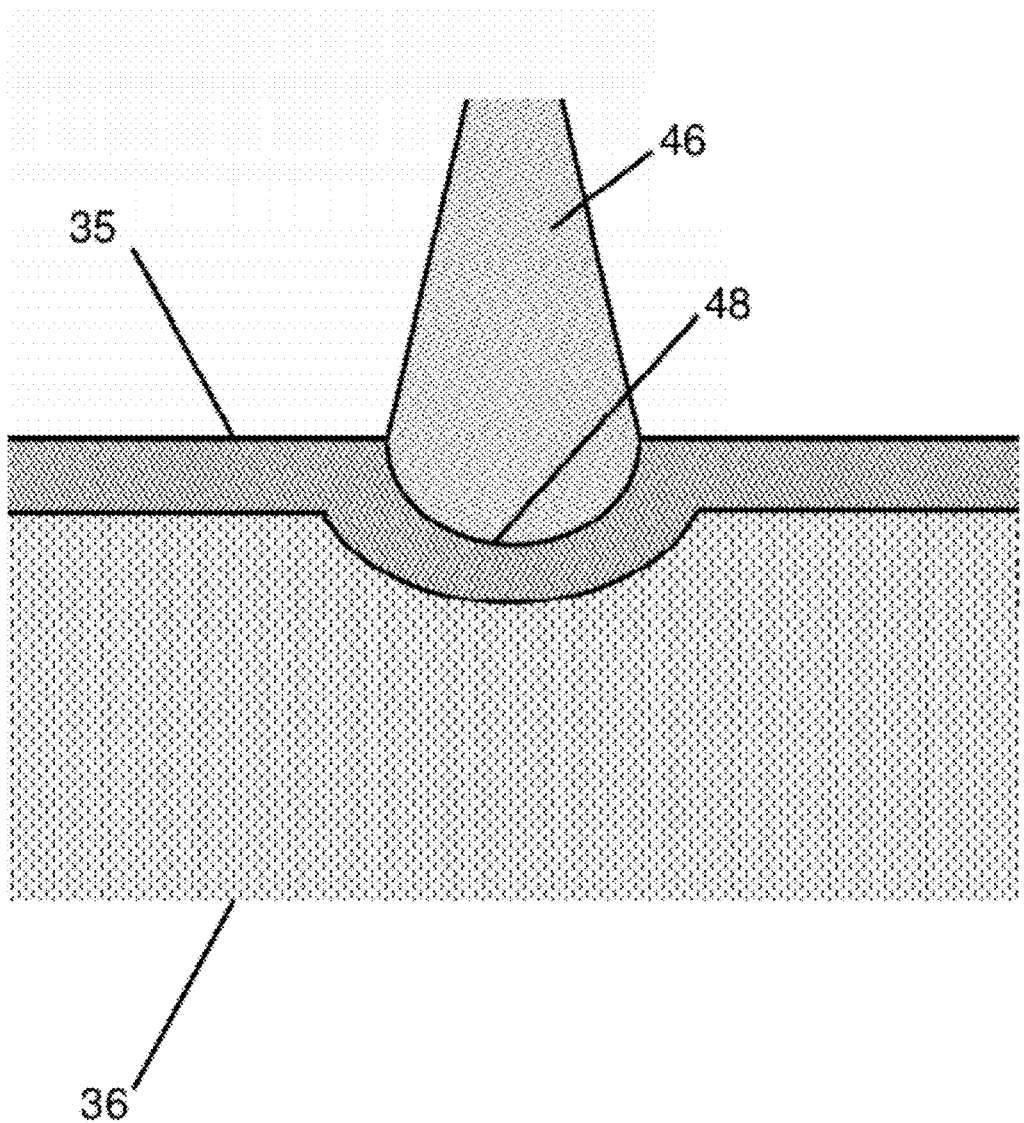
FIG. 6 shows a schematic representation of an air jet and a polymer film on a photovoltaic module during a non-contact recovery test according to one embodiment of the present invention.
Figure 7:
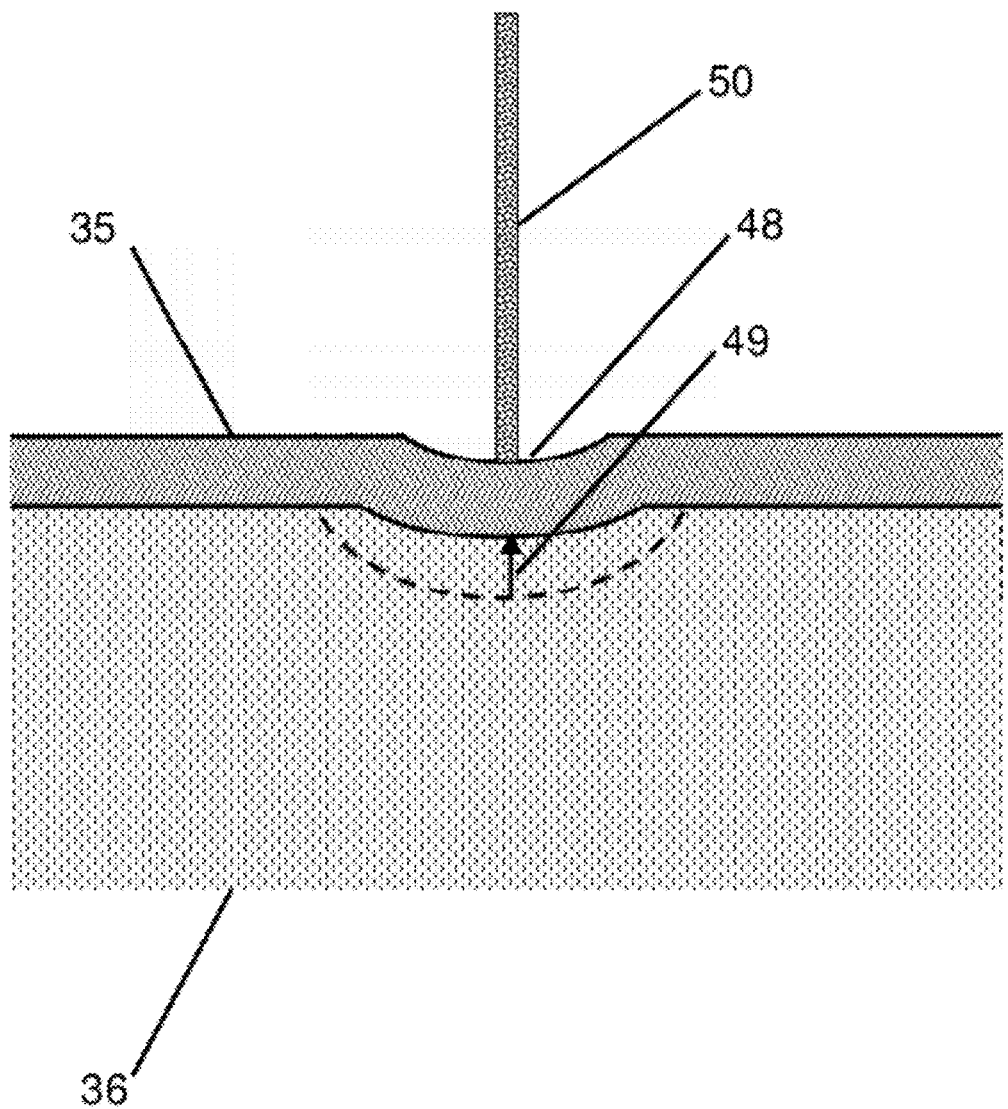
FIG. 7 shows a schematic representation of a laser interferometer measuring displacement recovery during a non-contact recovery test according to one embodiment of the present invention.

FIGS. 6 and 7 are directed to another embodiment of a recovery test similar to that described in Example 4. The material behavior and analysis is the same as in Example 4. However, the recovery test is performed without physically contacting the sample. FIG. 6 shows a thin backsheet 35 with an underlying EVA encapsulation film 36 on a surface. The film 36 has been deformed by an air jet 46 to form indentation 48. FIG. 7 shows the displacement recovery of indentation 48 in film 36. The amount of recovery is depicted as an arrow 49 between the dashed line and indentation 48. The displacement versus time is monitored using a laser interferometer. The laser interferometer is depicted as laser beam 50 in FIG. 7.

Example 7

Stress Relaxation Test Results

Stress relaxation tests were performed on small test samples representing a typical photovoltaic module stack, except without cells. The stack consisted of two sheets of EVA laminated between 3"×3" solar glass and assorted backsheets. Samples were laminated with EVA encapsulant at varying temperatures and times, thus providing test samples with differing amounts of gel content. Additional EVA material was laminated with each batch of test samples, for which the gel content was determined using the standard solvent extraction method with toluene. These gel content measurements provided reference gel content values for the samples.

Figure 8:
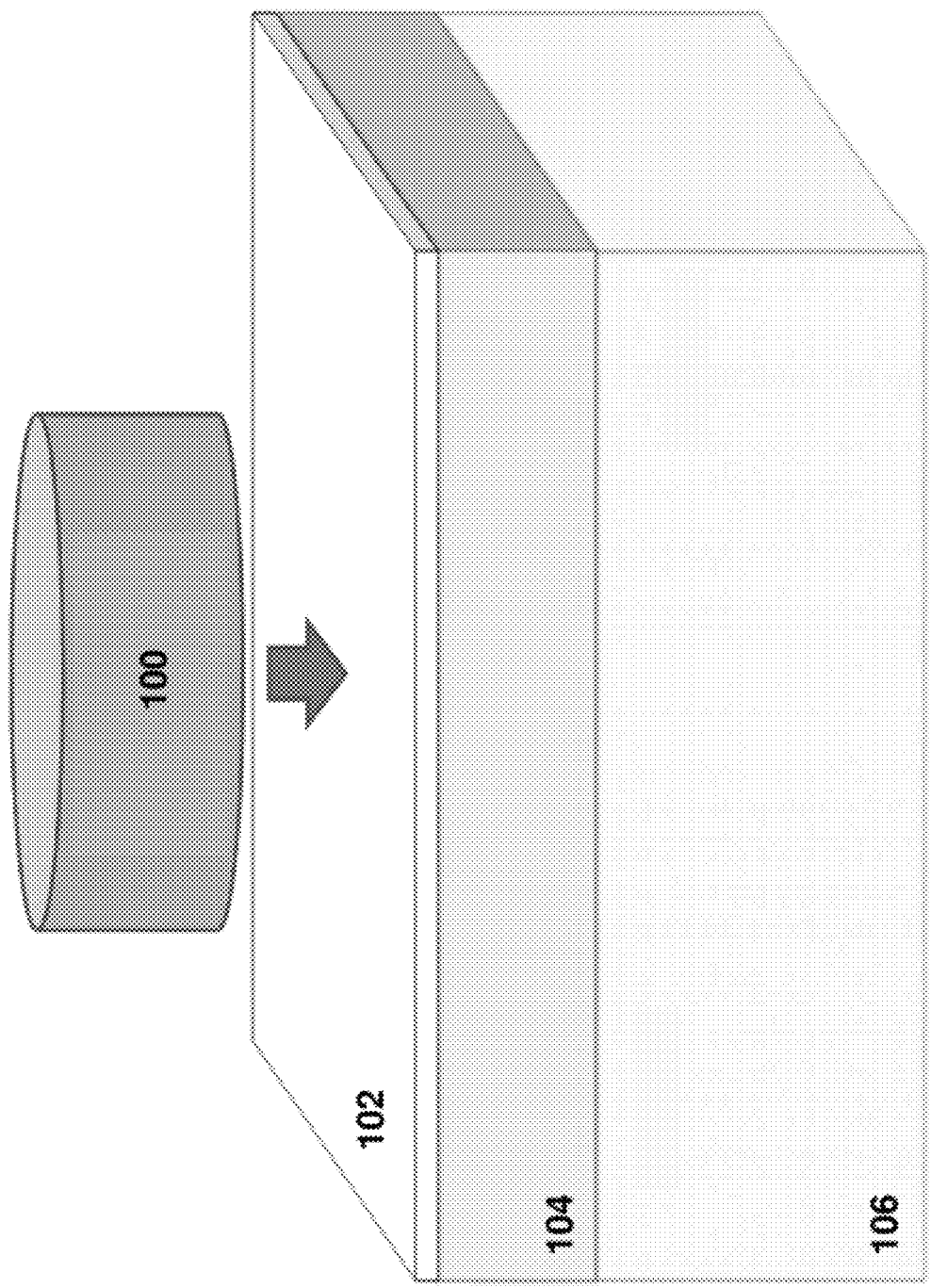
FIG. 8 shows a schematic representation of a stress relaxation or recovery tester and a photovoltaic module according to one embodiment of the present invention.

A schematic representation of an indenter head 100 and the upper layers of a test sample are shown in FIG. 8. As shown in the figure, the indenter head, is a cylinder with a flat contact area. For the present testing the contact area had a 4 mm diameter. During testing the indenter head was indented into a backsheet 102, as indicated by the arrow. The backsheet may be made out of any appropriate material, and typical thicknesses are approximately around 100 µm to 500 µm though the current disclosure is not limited to these specific values. A layer of EVA encapsulant 104 was provided beneath the backsheet and had an approximate thickness of 800 µm. Beneath the EVA encapsulant was glass 106.

While certain dimensions and configurations are stated above, other embodiments are envisioned. For example, in other embodiments, indenter head 10 may be a sphere, a hemisphere, a wedge, a dome, a pyramid, or any other appropriate geometry. Furthermore, the contact area between the indenter head and sample may be approximately 1 mm$^2$, 2 mm$^2$, 5 mm$^2$, 10 mm$^2$, 15 mm$^2$, 30 mm$^2$, or any other appropriate size. Alternatively, the contact area between the indenter head and sample may be a variable function dependent on the depth of indentation as would be expected for indenter heads with a non-constant profile such as the sphere, hemisphere, wedge, dome, or pyramid noted above. Additionally, while a backsheet thickness of approximately 250 µm was given, it is possible that other thicknesses could be used including, but not limited to, approximately 100 µm, 200 µm, 300 µm, 400 µm, 500 µm, or any other appropriate thickness. In some instances, a single layer, two layers, three layers, or any appropriate number of layers of encapsulant may be used during a lamination process.

Two commercially available formulations of EVA from two separate manufacturers were used for the EVA encapsulant during the study, along with four different commercially available backsheet materials. The back sheet materials were: polyvinyl fluoride/polyethylene terephthalate/ethylene vinyl acetate (TPE), polyethylene terephthalate (PET), polyamide (AAA), and polyvinyl fluoride/aluminum/polyethylene terephthalate/ethylene vinyl acetate (TAPE). These materials, their manufacturer, and their approximate thicknesses are summarized in Tables 1 and 2 below.

TABLE 1

| Manufacturer | EVA Material | Thickness |
|---|---|---|
| STR | Photocap 15420P EVA encapsulant | 420 µm |
| Etimex | VistaSolar 520.43 EVA encapsulant | 460 µm |

TABLE 2

| Manufacturer | Backsheet Material | Thickness |
|---|---|---|
| Dunmore | DUN-SOLAR TPE backsheet | 268 µm |
| Isovoltaic | Icosolar AAA backsheet | 250 µm |
| Mitsubishi | WSAC PET backsheet | 254 µm |
| Dunmore | DUN-SOLAR TAPE backsheet | 425 µm |

After producing the samples, a fully automated indentation test was performed using a Mark-10 ESM-301L stress-strain test stand using custom control software written in LabVIEW. A custom aluminum sample stage was constructed to accommodate an analog hotplate for steady state elevated temperature testing. A Parker linear stage was added to allow for multiple indentation locations with automated test position advancement. Similar to the one shown in FIG. 8, an indenter tip with a cylindrical stainless steel tip with a 4 mm diameter contact area was attached to a Mark-10 Series 5 force gauge on the test stand crosshead.

The crosshead was controlled to slowly approach the sample surface at approximately 0.5 mm/min. After a specified initial threshold force reading of 0.02 N, corresponding to initial contact with the backsheet, the control software initiated a rapid indentation into the backsheet at 100 mm/min to a depth of approximately 100 µm. In other embodiments the cross head may initially approach the surface at speeds less than approximately 0.01 mm/min, 0.1 mm/min, 1 mm/min, 10 mm/min, or any other appropriate speed. In yet another embodiment, the initial threshold force reading may be less than approximately 0.01 N, 0.1 N, 1 N, or any other appropriate threshold. Furthermore, the rapid indentation speed may be approximately 10 mm/min, 100 mm/min, 1,000 mm/min, 2,000 mm/min, 5,000 mm/min, 10,000 mm/min, or any other appropriate speed. In addition, the sample may alternatively be indented to a depth of approximately 200 µm, 300 µm, 400 µm, 500 µm, or any other appropriate depth.

After indentation, the indenter was held stationary for several minutes to measure the decaying compressive force. Each sample was indented at several different locations and up to five times at each location, in order to account for measurement error and sample variability. In addition, the indentation stress relaxation tests were performed at ambient temperature, 50° C., and 80° C. because the mechanical properties of EVA are known to vary with temperature. The temperature of the samples was monitored using an IR camera and thermocouples embedded in similar samples adjacent to the sample under test.

The data collected during these stress relaxation measurements consisted of readings on the force gauge over a period of several minutes, with a temporal resolution of 20-50 ms. Data analysis and curve fitting demonstrated that the stress relaxation curves featured multiple time constants, as described by the generalized Maxwell model for viscoelastic polymers:

$$\sigma(t) = a_1 e^{\frac{-t}{\tau_1}} + a_2 e^{\frac{-t}{\tau_2}} + a_3 e^{\frac{-t}{\tau_3}} + \ldots + \sigma_0 \tag{1}$$

where $\sigma(t)$ is the stress as a function of time t, $\sigma_0$ is the residual elastic stress after infinite time, and $\{a_i, \tau_i\}$ are the empirical parameters describing exponential decay processes.

Figure 9:
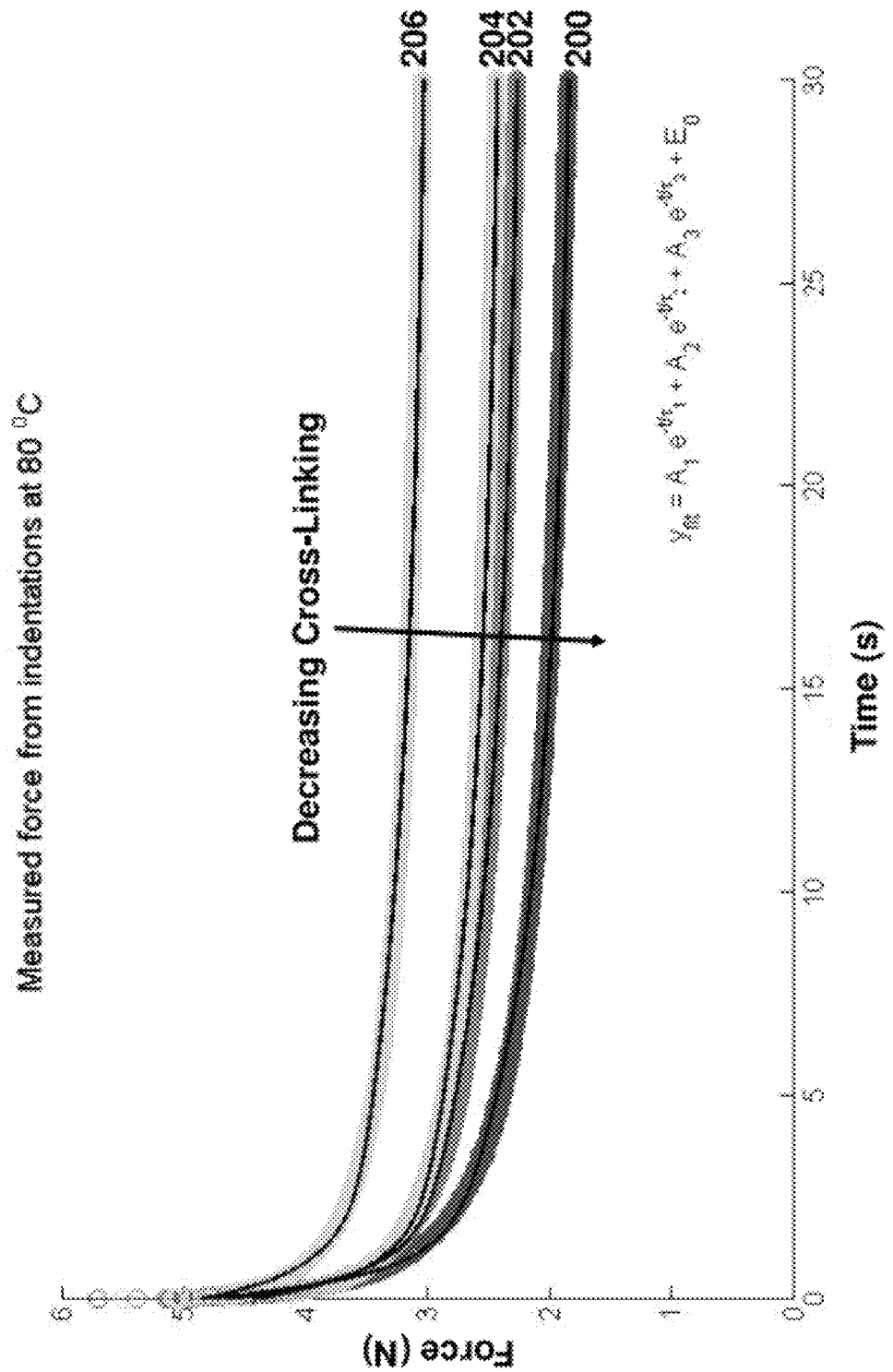
FIG. 9 shows a graph depicting stress relaxation for materials with different amounts of cross-linking.

FIG. 9 presents a graph of the stress relaxation curves versus time for samples with different levels of cross-linking. Testing was conducted at 80° C. Curve 200 corresponds to a 31% gel content. Curve 202 corresponds to a 64% gel content. Curve 204 corresponds to a 84% gel content. Curve 206 corresponds to a 90% gel content. The recorded data is indicated by the large gray lines and the fit three term exponential generalized Maxwell models are indicated by the overlaying thin black lines. To get a good estimate of the time constants, data was collected for about 30 sec to 60 sec. Decreasing cross-linking versus the curves is indicated by the arrow. The fitted curves match the data well, as shown in the figure. The calculated values for each parameter in the fitting functions are shown with respect to the sample cross-linking level in Table 3. The data indicate an increase in all time constants and a decrease in all pre-exponential constants as the level of cross-linking increases. Thus, the fit parameters may be used to distinguish between different levels of cross-linking within a sample. In some embodiments, a single fit parameter may be compared or multiple parameters may be compared. Without wishing to be bound by theory, the implication of these observed trends is that uncross-linked samples have a deep force decay curve, while highly cross-linked samples have a shallow force decay curve. These observations are consistent with the interpretation of hindered chain motion leading to slower stress relaxation which implies longer relaxation times and correspondingly higher time constants.

TABLE 3

| | Gel Content | | | |
|---|---|---|---|---|
| Parameter | 31% | 64% | 84% | 90% |
| $A_1$ [N] | 1.9 | 1.5 | 1.2 | 1.1 |
| $T_1$ [s] | 0.56 | 0.58 | 0.64 | 0.75 |
| $A_2$ [N] | 1.0 | 0.82 | 0.71 | 0.64 |
| $T_2$ [s] | 6.8 | 7.4 | 8.0 | 9.1 |
| $A_3$ [N] | 0.45 | 0.45 | 0.39 | 0.38 |
| $T_3$ [s] | 82 | 92 | 97 | 124 |
| $y_\infty$ [N] | 1.5 | 1.9 | 2.1 | 2.7 |

While the fit parameters were found to be able to distinguish between different levels of cross linking, a measurement time on the order of 30 sec to 60 sec was used to determine the decay constants. In addition to the above, it was observed in FIG. 9 that the force decay amplitude, i.e. the total drop in force, during the stress relaxation measurement was greatest for the samples with lower levels of cross-linking. Furthermore, the majority of force decay occurred within approximately the first 5 seconds of testing. Therefore, a more rapid measurement technique may be implemented using the observed force decay to distinguish between different cross-linking levels, wherein the force decay amplitude may be correlated with the gel content. In view of the above, in a preferred embodiment, the test method may include performing a relaxation measurement on a sample and observing the force decay versus time. After a predetermined time has elapsed, the observed force decay may be compared with a calibration to determine a gel content of the material. In some embodiments the measurement may take approximately 1 sec, 2 sec, 5 sec, 10 sec, 30 sec, or any other appropriate time period.

Example 8

Comparative Testing of Measurement Temperature

The analysis presented below focuses on the decay force amplitude at t=5 s after the indentation depth is reached, but the results can also be generalized to times ranging at least from approximately t=1 s to t=30 s. It is also envisioned, that decay force amplitudes for times less than 1 second may also be used for different testing geometries and/or materials.

Figure 10:
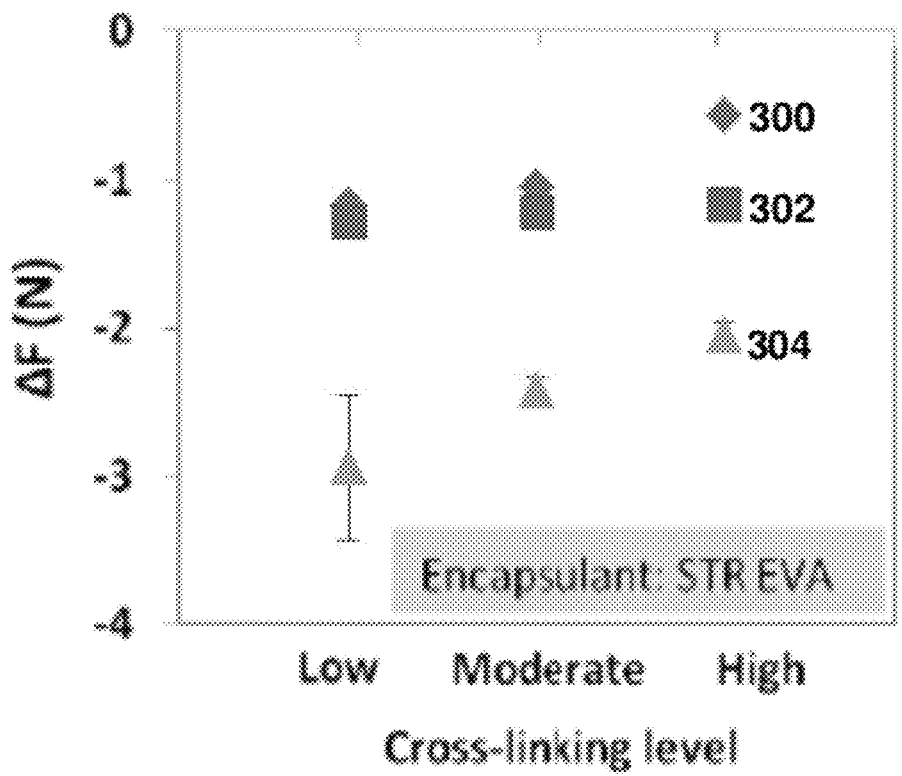
FIG. 10 shows a graph of the force decay amplitude during stress relaxation measurements for different temperatures and amounts of cross-linking for STR EVA encapsulant.
Figure 11:
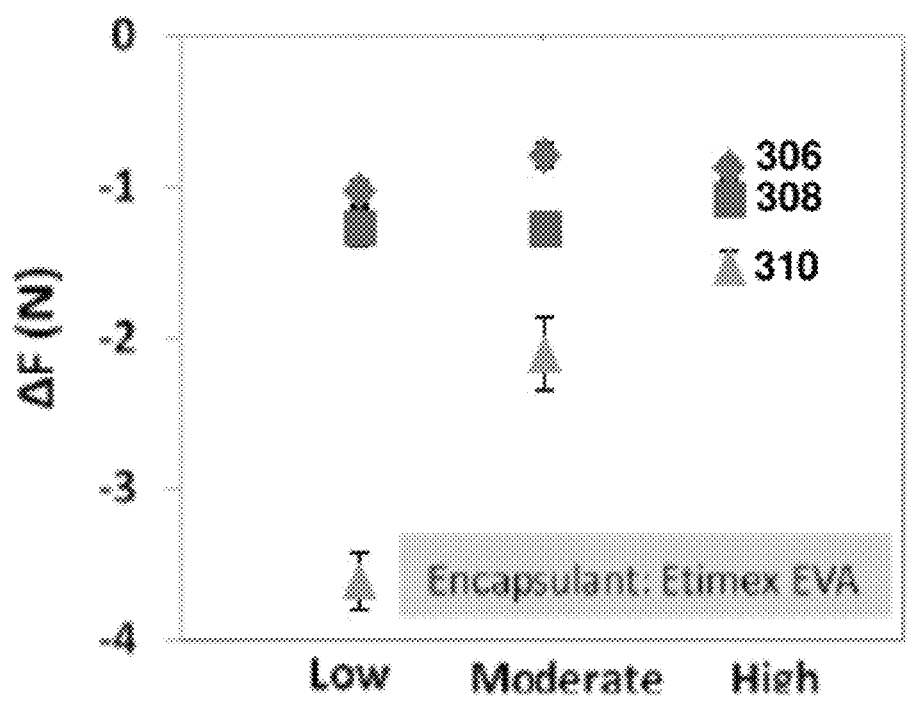
FIG. 11 shows a graph of the force decay amplitude during stress relaxation measurements for different temperatures and amounts of cross-linking for Etimex EVA encapsulant.

In order to demonstrate the robust nature of the stress relaxation method for distinguishing EVA cross-linking levels in module samples, the indentation tests were repeated on samples with a variety of common module materials. FIGS. 10 and 11 show a comparison of the force decay amplitude measured at 5 seconds for EVA encapsulants from two different manufacturers, Etimex and STR, at 23° C., 50° C., and 80° C. These figure also illustrate the effect of test temperature on the distinguishability of cross-linking levels. The approximate gel content levels of the samples as measured by gel fraction was 0%-31% for low, 64% for moderate, and 80%-84% for high. The sample points are based on nine repeated measurements on each sample, with the error bars representing 95% confidence intervals.

FIGS. 10 and 11 show a comparison of force decay amplitudes of samples with different levels of cross-linking at testing temperatures of 23° C., 50° C., and 80° C. Samples 300 correspond to STR EVA encapsulant tested at 23° C. Samples 302 correspond to STR EVA encapsulant tested at 50° C. Samples 304 correspond to STR EVA encapsulant tested at 80° C. Samples 306 correspond to Etimex EVA encapsulant tested at 23° C. Samples 308 correspond to Etimex EVA encapsulant tested at 50° C. Samples 310 correspond to Etimex EVA encapsulant tested at 80° C.

As illustrated in FIGS. 10 and 11, at 80° C., all three cross-linking levels are statistically distinguishable above the 95% confidence level in each material system (analysis based on a one-tailed t-test of nine repeated indent measurements per sample). Furthermore, the force decay amplitude effects were found to be amplified at elevated temperatures, such as would be experienced by modules shortly after vacuum lamination during the manufacturing process. As a result, without wishing to be bound by theory, the disclosed method for cross-linking measurement may be increasingly effective at higher temperatures. While, the disclosed method may become more effective at elevated temperatures, it may also be desirable to maintain the testing temperatures below the decomposition temperature of the polymers and/or below a threshold temperature that may damage components internal to, or integral with, the structure, or component, being measured. In view of the above, a preferred test temperature may be 80° C. In other embodiments, the test may be conducted at approximately room temperature, 40° C., 60° C., 100° C., or any other appropriate temperature. While certain temperatures have been given for testing, it should also be understood that the optimal testing temperature will vary from material to material and could be readily determined by one of skill in the art. Therefore, other temperatures are envisioned for testing in addition to the above as the current disclosure is not limited in this fashion.

Example 9

Comparative Testing of Module Materials

Figure 12:
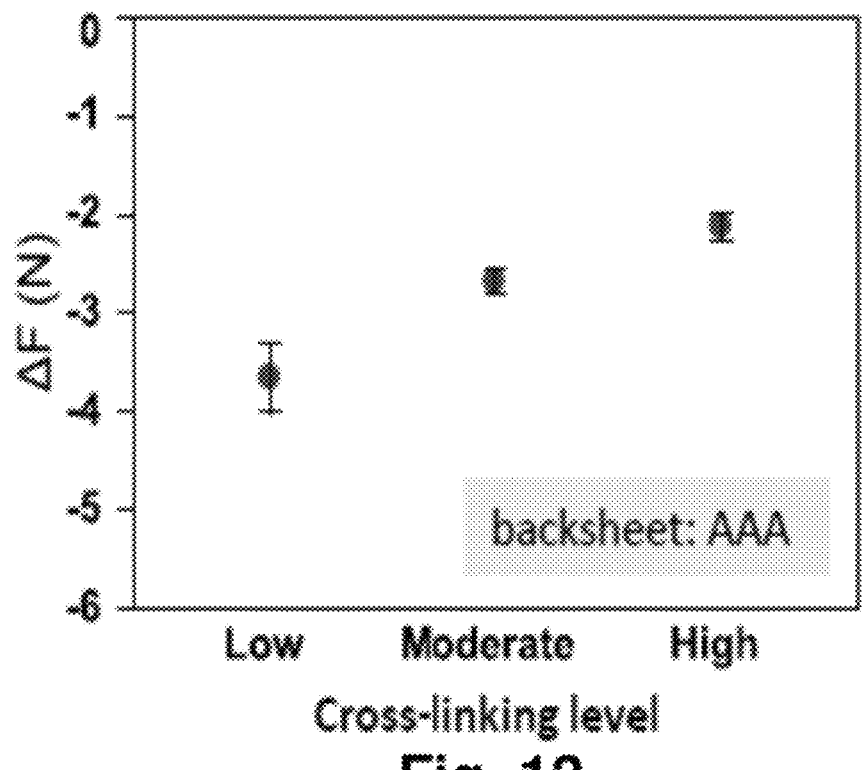
FIG. 12 shows a graph of the force decay amplitude during stress relaxation measurements for different amounts of cross-linking for STR EVA encapsulant and an AAA backsheet.
Figure 13:
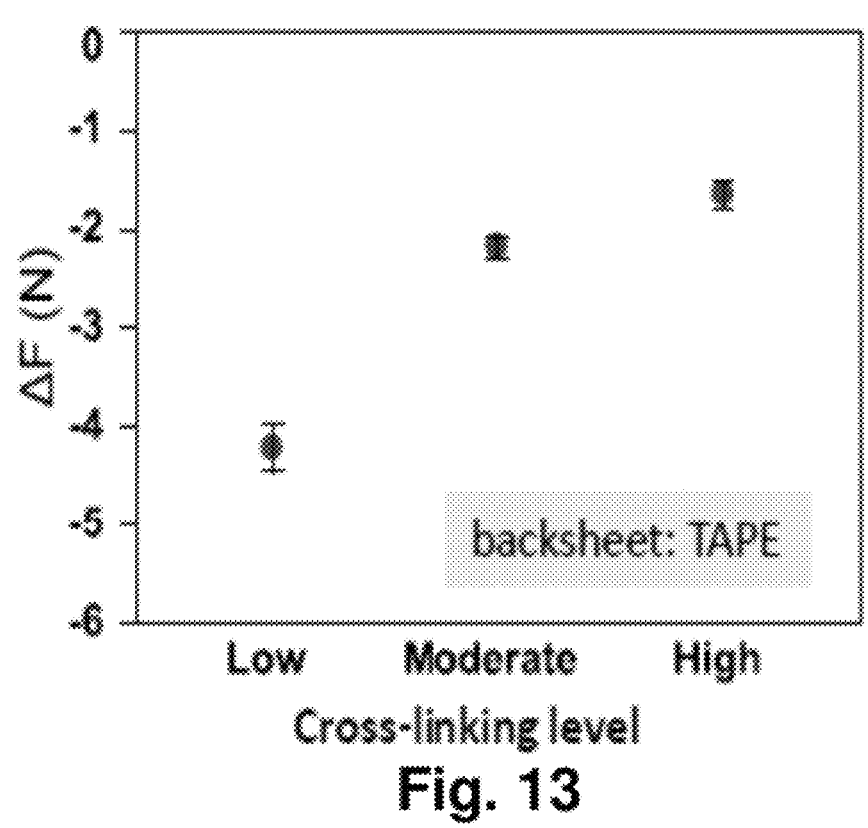
FIG. 13 shows a graph of the force decay amplitude during stress relaxation measurements for different amounts of cross-linking for STR EVA encapsulant and a TAPE backsheet.
Figure 14:
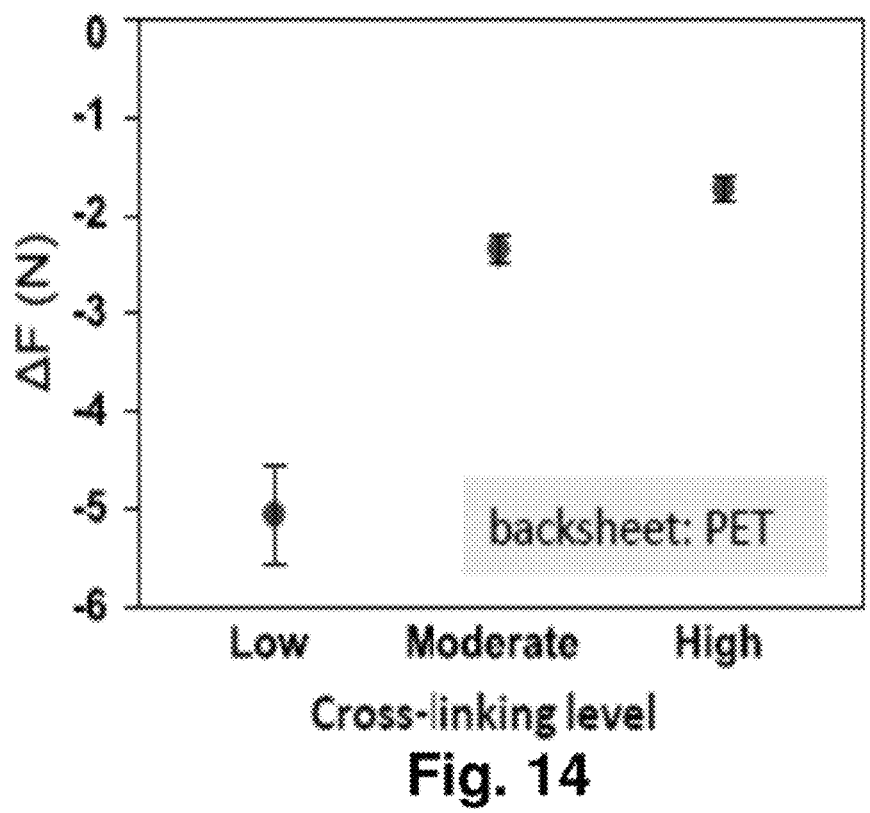
FIG. 14 shows a graph of the force decay amplitude during stress relaxation measurements for different amounts of cross-linking for STR EVA encapsulant and an PET backsheet.
Figure 15:
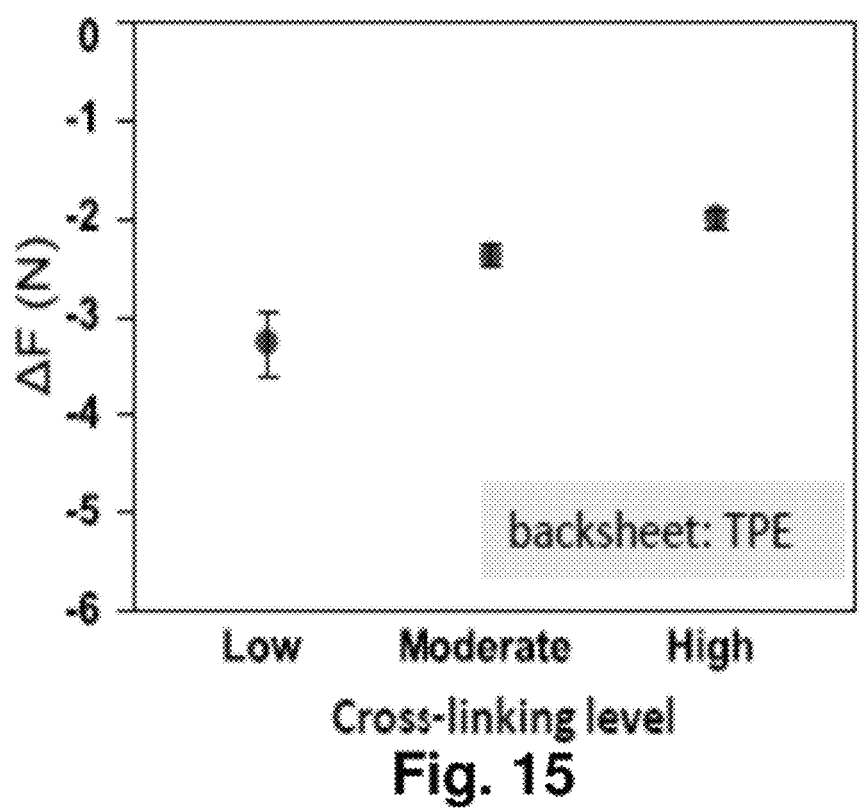
FIG. 15 shows a graph of the force decay amplitude during stress relaxation measurements for different amounts of cross-linking for STR EVA encapsulant and an TPE backsheet.

Additional stress relaxation testing was conducted for test samples with a variety of common photovoltaic module backsheet materials applied to EVA encapsulant with low, medium, and high levels of cross-linking. The approximate gel content levels of the samples as measured by gel fraction was 0% for low, 64%-66% for moderate, and 81% for high. The sample points are based on nine repeated measurements on each sample, with the error bars representing 95% confidence intervals. Testing was conducted at 80° C. FIGS. 12-15 show a comparison of four different backsheet types. FIG. 12 corresponds to STR EVA laminate with a AAA backsheet. FIG. 13 corresponds to STR EVA laminate with a TAPE backsheet. FIG. 14 corresponds to STR EVA laminate with a PET backsheet. FIG. 15 corresponds to STR EVA laminate with a TPE backsheet. Once again, all the gel content levels were statistically distinguishable above the 95% confidence level for the four different backsheets at the tested temperature of 80° C.

FIGS. 12-15 also illustrate that the separate material system exhibit similar behaviors and force decay amplitudes. However, there are differences between the absolute values noted. Consequently, for accurate measurements of gel content level, a specific calibration curve may be determined for specific materials and/or constructions. Alternatively, since the different materials behave similarly, a generic calibration may be provided that is an average of typical modules, or other appropriate systems, that will be tested. Thus, a user may either choose to create a more accurate specific calibration for testing, or may instead use a less accurate, but still applicable general calibration.

Example 10

Storage Modulus vs. Temperature

Figure 16:
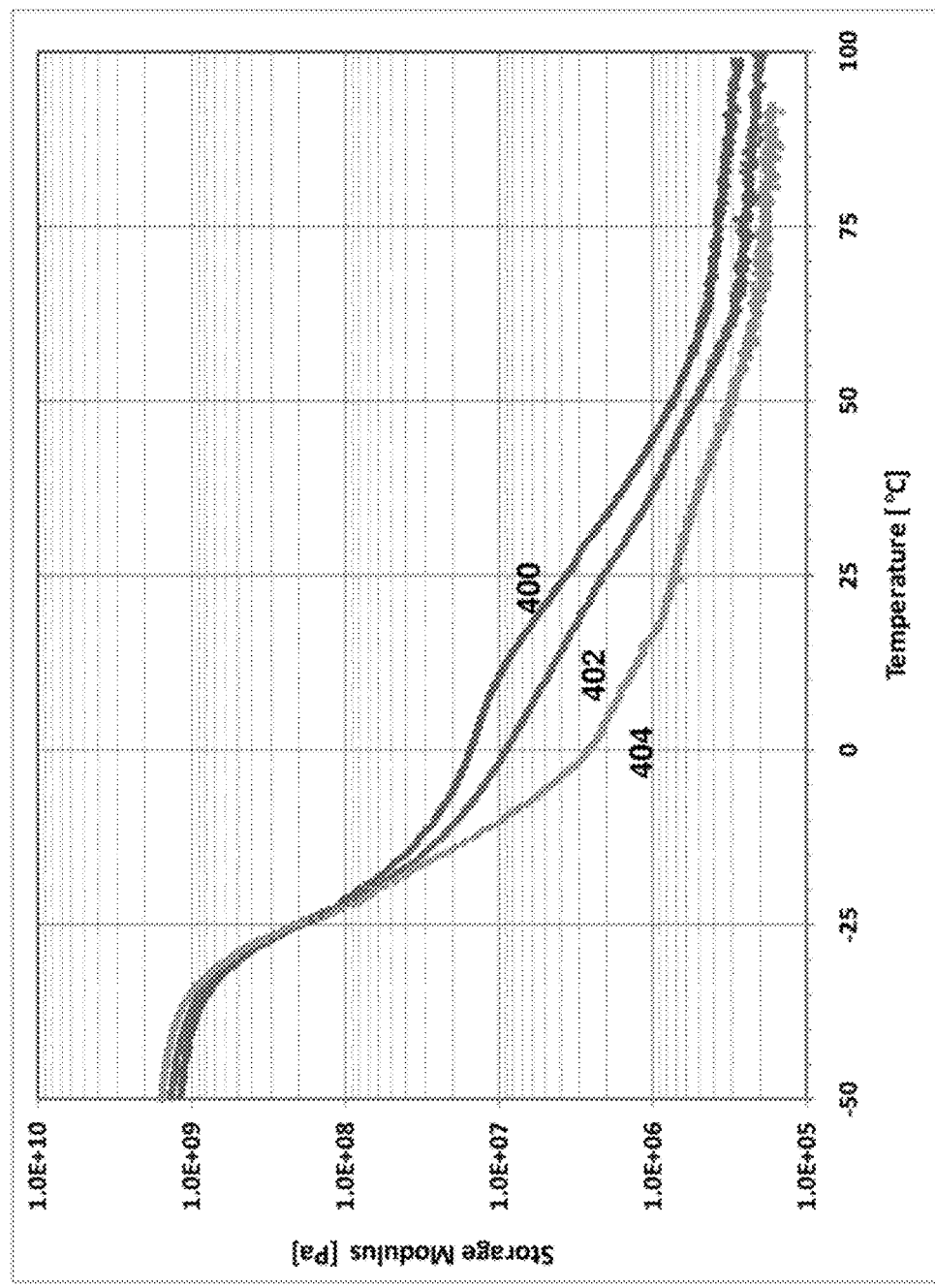
FIG. 16 shows a graph of dynamic mechanical analysis measurements for three samples obtained from the same sheet of cured EVA.
Figure 17:
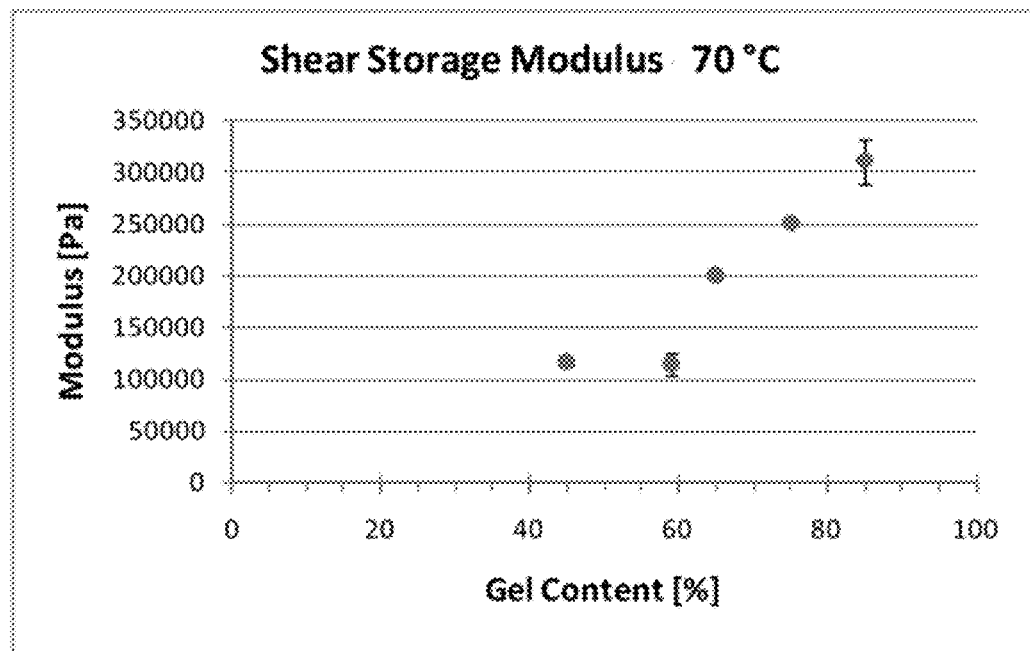
FIG. 17 shows a graph of Shear Storage Modulus of bare EVA samples versus gel content measured at 70° C.
Figure 18:
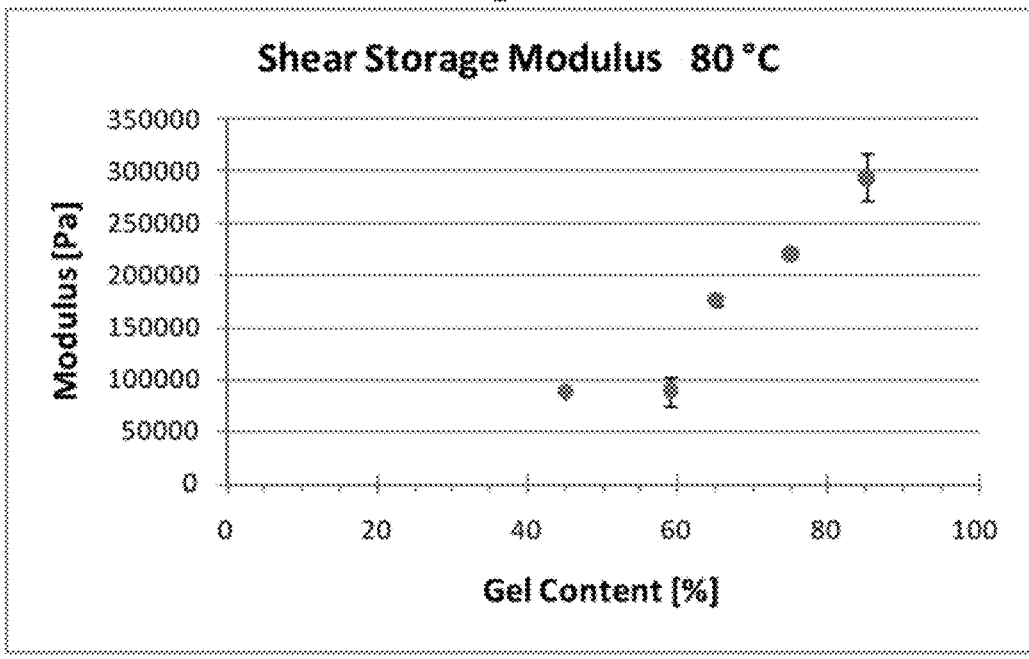
FIG. 18 shows a graph of Shear Storage Modulus of bare EVA samples versus gel content measured at 80° C.
Figure 19:
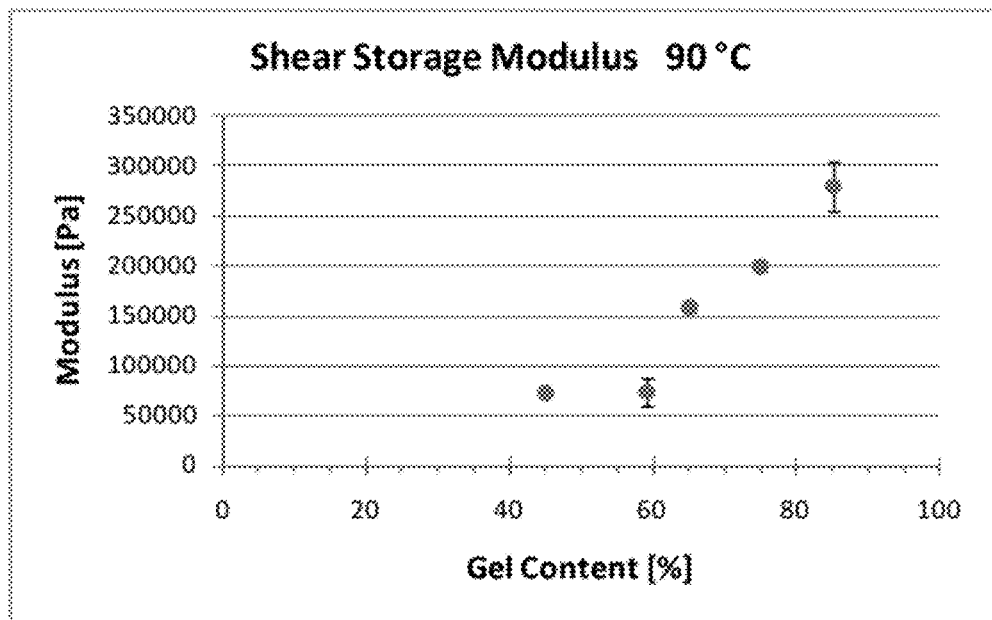
FIG. 19 shows a graph of Shear Storage Modulus of bare EVA samples versus gel content measured at 90° C.
Figure 20:
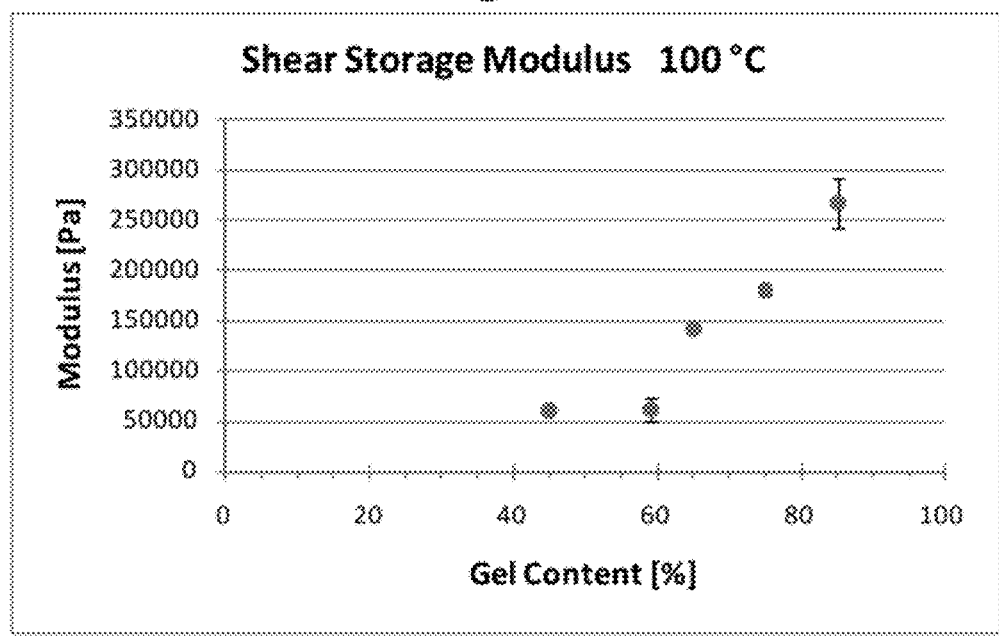
FIG. 20 shows a graph of Shear Storage Modulus of bare EVA samples versus gel content measured at 100° C.
Figure 21:
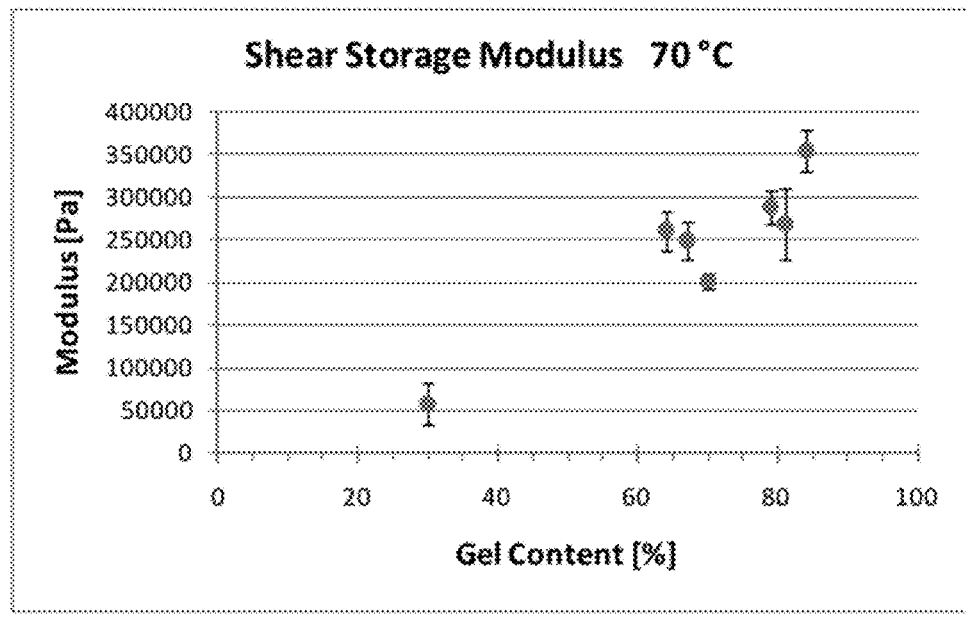
FIG. 21 shows a graph of Shear Storage Modulus of EVA samples with a back sheet versus gel content measured at 70° C.
Figure 22:
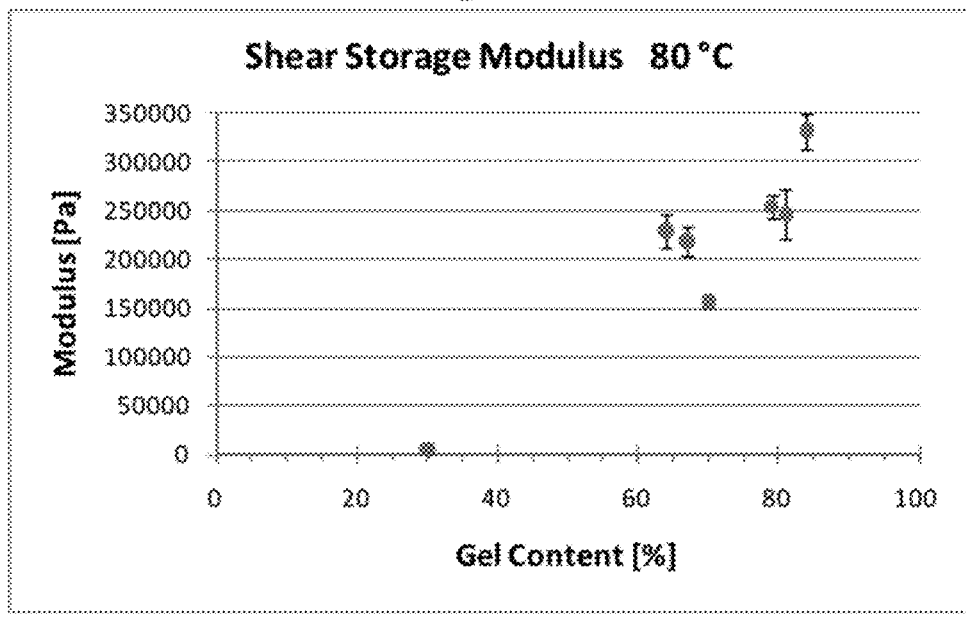
FIG. 22 shows a graph of Shear Storage Modulus of EVA samples with a back sheet versus gel content measured at 80° C.
Figure 23:
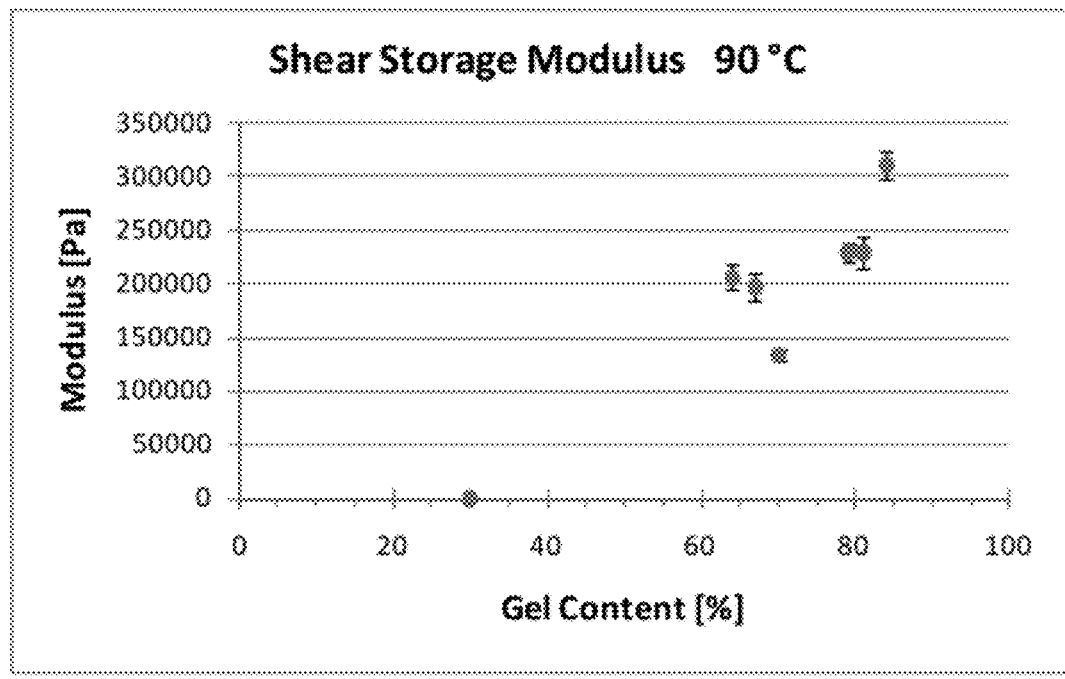
FIG. 23 shows a graph of Shear Storage Modulus of EVA samples with a back sheet versus gel content measured at 90° C.
Figure 24:
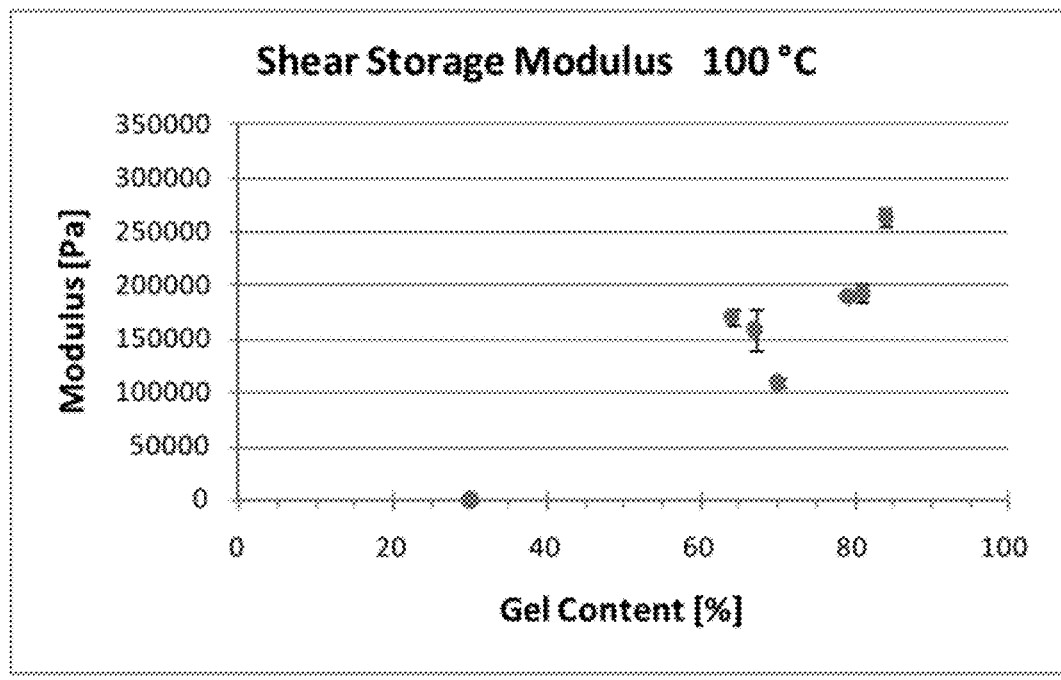
FIG. 24 shows a graph of Shear Storage Modulus of EVA samples with a back sheet versus gel content measured at 100° C.

Without wishing to be bound by theory, the above noted improved distinguishability of cross-linking level versus increasing temperature may be correlated with lower levels of variability in the value of the storage modulus of cross-linked EVA samples above about 65° C. It is presumed that the higher variability in the storage modulus below approximately 65° C. is a result of local variations in the material properties. To illustrate this phenomenon three samples were cut from a single sheet of EVA with a gel content greater than 80%. The samples were tested in a dynamic mechanical analyzer to determine the storage modulus of each sample between approximately −50° C. and 100° C., see FIG. 16. Without wishing to be bound by theory, the local variation in properties may be due to differences in the local cooling rate of the material after curing which may lead to local variations in the stored energy, and thus configurational state, of the material. When the materials go through the glass transition at approximately −20° C. to −15° C., as indicated by the inflection in the curves at that temperature as illustrated in FIG. 16, the material is able to relax on a laboratory time scale. Once the materials have reached approximately 65° C. the different samples have relaxed to approximately equivalent states and thus have approximately equivalent Storage Moduli. Variations between the samples may also be due to local variations in material composition. However, regardless of the physical phenomenon occurring, above approximately 65° C., all thermal transitions appear to be complete and the samples have reached a plateau modulus. As a result, indentation measurements made above this temperature for EVA may be expected to provide information solely based on the cross-link density of the polymer. It should be noted that the current disclosure is not limited to testing above, below, or at 65° C. as this temperature is tied to a specific material and a specific construction. As such, appropriate testing temperatures should be determined for the specific material and/or construction being evaluated and would be easily determined by one of skill in the art.

Example 11

Dynamic Mechanical Analyzer Test Results

Shear mode dynamic mechanical analysis (DMA) measurements on cross-linked EVA were performed on a Perkin-Elmer DMA8000. The measurements were performed over a temperature range from ambient to 100° C. The test specimens were 6.5 mm diameter disks punched from EVA samples that were cured under various process conditions in the laminator to achieve different levels of cross-linking. The results on the bare EVA samples are presented in FIG. 17-21 corresponding to temperatures of 70° C., 80° C., 90° C., and 100° C. respectively. The presented results are average values measured on three specimens and the error bars represent 95% confidence level. The data show that above approximately 60% gel content, the degree of cross-linking can be readily distinguished based on the value of the shear storage modulus. In addition, the effect is observed at each of the four different temperatures tested. It is also interesting to note, that the shear modulus at 45% and 59% gel content is nearly identical. Without wishing to be bound by theory, this is consistent with the "rule-of-thumb" that a minimum 65% gel content is required for proper lamination of EVA, since below 60% gel content, the samples behave identically (i.e. the shear modulus is low and the EVA encapsulant will have a propensity to creep, regardless of the actual gel content). In view of the above, shear measurements to determine the shear modulus may offer an alternative to the indentation testing detailed above. While, specific temperatures and gel fractions have been stated with respect to the EVA encapsulant, these temperatures and threshold gel contents may change with different materials. Consequently, the current disclosure should not be limited to EVA and its behavior, and instead should be viewed generally as indicating shear measurements may be used to determine the level of cross-linking in a polymeric material.

To ensure that the above detailed technique could be applied to a fully laminated photovoltaic modules, without the need to cut out a sample of EVA, the shear measurements were repeated on a material stack that included a backsheet material. Multiple 6.5 mm specimens were punched from EVA/backsheet samples and measured in shear mode in a DMA. The results are depicted in FIGS. 21-24 and correspond to 70° C., 80° C., 90° C., and 100° C. respectively. The presented results are average values measured on three specimens and the error bars represent 95% confidence level. The observed results are approximately linear with respect to degree of cross-linking/gel content. As in the bare EVA testing above, the different cross-linking levels were readily distinguished at each temperature, although the confidence level error bars were larger, particularly at the lower temperatures. The decrease in the confidence level was due to an increase in the signal to noise ratio. Without wishing to be bound by theory, this may be due to the inclusion of the backsheet. More specifically, the measurement could include contributions from the adhesion or adhesion surface layer between the EVA and backsheet. Additionally, the backsheet, which is smooth, could cause the platens to slip on the surface.

In view of the above, shear measurements are capable of differentiating between different curing levels, even when a backsheet is present. It should be noted, testing conducted below 70° C. in the current testing was unable to differentiate between the different levels of cross-linking. Without wishing to be bound by theory, the shear measurement may have been unable to differentiate between the different levels of cross-linking below 70° C. due to the increased stiffness of the material at lower temperatures. However, the current disclosure should not be limited to temperatures above 70° C. since the use of different materials and/or constructions may lead to temperatures above, or even below, 70° C. being applicable for shear measurements to determine the level of cross-linking.

Example 12

Evaluation of Non-Destructive Test Results

In order to determine whether the modules would be damaged as a result of indentation testing, several single cell mini-modules were made. The different samples were then either fully cured or minimally cured for comparative testing purposes. The samples were subjected to indentations at displacement depths of 100 µm, 200 µm, 300 µm, and 400 µm. The tests were conducted both at room temperature and at 80° C., and indentations were made both on the active area of the cell and directly behind the busbar, where the stress is expected to be greatest. Electroluminescence (EL) images, corresponding to FIGS. 25-28, were taken using a Xenics Xeva 1151 InGaAs camera before and after multiple indentations to demonstrate the non-destructive nature of the indentation tests. FIG. 25 depicts a low gel content module prior to indentation and FIG. 26 depicts the same module after indentation. FIG. 27 depicts a high gel content module prior to indentation and FIG. 28 depicts the same module after indentation.

Examination of mini-modules with EL imaging before and after various indentation tests indicated that the test process is well within non-destructive limits. No cell breakage was observed in testing, even for the 400 µm depth indentations. Fracture of the cells was only observed for loads greater than 500 N, whereas typical forces measured during indentations up to 400 µm were all under 20 N. Furthermore, visual inspection of the samples revealed no obvious damage to the integrity of the backsheet, such as punctures or pinholes.

CONCLUSION

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

In the above specification the terms force and displacement are used. It is to be understood that these terms may be interchangeably used with the terms stress and strain respectively. Furthermore, certain embodiments describe methods or apparatuses acting on a polymer sample or an EVA encapsulating film. The methods and apparatuses described above are capable of working with both polymer samples or the described EVA encapsulating film. The specification therefore does not exclude a method or apparatus described with a polymer sample from use with an EVA encapsulating film and visa versa.

The above-described embodiments of the invention can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention, e.g., the reference information relating to a degree of cross-linking in a polymer, may be embodied at least in part as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A method for detecting cross-linking in a polymer sample, the method comprising:
   A) physically deforming a polymer sample using a tester;
   B) obtaining sample information relating to a relaxation or a recovery of the polymer sample in response to A); and
   C) comparing the sample information to reference information relating to the cross-linking so as to determine a degree of the cross-linking in the polymer sample.

2. The method of claim 1, wherein the sample information obtained in B) includes at least one of a relaxation time constant, a force decay, a force, a displacement, and a time.

3. The method of claim 1, wherein A) further comprises deforming a surface of the polymer sample to an approximate depth of 0.2 mm.

4. The method of claim 1, wherein A) comprises deforming the polymer sample to a constant deformation.

5. The method of claim 1, wherein A) comprises deforming the polymer sample via an applied force and removing the applied force after deformation.

6. The method of claim 1, wherein A) comprises applying an oscillating deformation to the polymer sample.

7. The method of claim 1, further comprising performing A) and B) at an elevated temperature.

8. The method of claim 1, wherein A) and B) are performed without physically contacting the polymer sample.

9. The method of claim 1, wherein A), B), and C) are performed in line with a laminator.

10. The method of claim 1, wherein A), B), and C) are performed in a laminator.

11. The method of claim 1, wherein A), B), and C) are performed without adversely affecting a relevant functionality of the polymer sample.

12. The method of claim 1, wherein A), B), and C) are performed without destroying the polymer sample.

13. An apparatus for detecting cross-linking in a polymer sample, the apparatus comprising:
   a tester comprising at least a first component to physically deform the polymer sample and a second component to obtain sample information regarding a physical response of the polymer sample to deformation; and
   a processor programmed to determine a degree of the cross-linking in the polymer sample at least in part by comparing the sample information to reference information relating to the cross-linking.

14. The apparatus of claim 13, wherein the physical response is a relaxation or recovery response.

15. The apparatus of claim 13, wherein the processor is programmed to determine at least one relaxation time constant from the information regarding the physical response of the polymer sample for comparison with the reference information.

16. The apparatus of claim 13, wherein the processor is programmed to determine at least one force decay from the information regarding the physical response of the polymer sample for comparison with the reference information.

17. The apparatus of claim 13, wherein the first component deforms the polymer sample to an approximate depth of 0.2 mm.

18. The apparatus of claim 13, wherein the first component deforms the polymer sample to a constant deformation.

19. The apparatus of claim 13, wherein the first component deforms the polymer sample via an applied force and removes the applied force after deformation.

20. The apparatus of claim 13, wherein the first component deforms the polymer sample by applying an oscillating deformation to the polymer sample.

21. The apparatus of claim 13, wherein the first member comprises an air jet.

22. The apparatus of claim 13, the first member comprises an indenter head.

23. The apparatus of claim 22, wherein the indenter head is approximately a 30 degree truncated wedge.

24. The apparatus of claim 13, wherein the second member comprises a laser interferometer.

25. The apparatus of claim 13, wherein the first component deforms the polymer sample in a non-destructive manner.

26. The apparatus of claim 13, wherein the apparatus is located in line with a laminator.

27. The apparatus of claim 13, wherein the apparatus is located inside of or is a part of a laminator.

28. A method for detecting cross-linking in an ethylene vinyl acetate copolymer film, the method comprising:
   A) physically deforming the film using a tester;
   B) obtaining sample information relating to a relaxation or a recovery of the film in response to A); and C) comparing the sample information to reference information relating to the cross-linking so as to determine a degree of the cross-linking in the film.

29. The method of claim 28, wherein the sample information obtained in B) includes at least one of a relaxation time constant, a force decay, a force, a displacement, and a time.

30. The method of claim 28, wherein A) further comprises deforming the film to an approximate depth of 0.2 mm.

31. The method of claim 28, further comprising performing A) and B) at an elevated temperature.

32. The method of claim 28, wherein A) and B) are performed without physically contacting the film.

33. The method of claim 28, wherein A), B), and C) are performed in line with a laminator.

34. The method of claim 28, wherein A), B), and C) are performed in a non-destructive manner with regards to the film.

35. An apparatus for detecting cross-linking in an ethylene vinyl acetate copolymer film, the apparatus comprising:
 a tester comprising at least a first component to physically deform the film and a second component to obtain sample information regarding the physical response of the film to deformation; and
 a processor programmed to determine a degree of the cross-linking in the polymer sample at least in part by comparing the sample information to reference information relating to the cross-linking.

36. The apparatus of claim 35, wherein the physical response is a relaxation or recovery response.

37. The apparatus of claim 35, wherein the processor is programmed to determine at least one relaxation time constant from the information regarding the physical response of the film for comparison with the reference information.

38. The apparatus of claim 35, wherein the processor is programmed to determine at least one force decay from the information regarding the physical response of the film for comparison with the reference information.

39. The apparatus of claim 35, wherein the first component deforms the film to an approximate depth of 0.2 mm.

40. The apparatus of claim 35, wherein the first member comprises an air jet.

41. The apparatus of claim 35, the first member comprises an indenter head.

42. The apparatus of claim 41, wherein the indenter head is approximately a 30 degree truncated wedge.

43. The apparatus of claim 35, wherein the second member comprises a laser interferometer.

44. The apparatus of claim 35, wherein the first component deforms the film in a non-destructive manner.

45. The apparatus of claim 35, wherein the apparatus is located in line with a laminator.

* * * * *